United States Patent
Huo

(10) Patent No.: US 11,103,141 B2
(45) Date of Patent: Aug. 31, 2021

(54) CORONARY ARTERY LOAD DETECTING SYSTEM AND METHOD

(71) Applicant: SUZHOU RAINMED MEDICAL TECHNOLOGY CO., LTD., Suzhou (CN)

(72) Inventor: Yunfei Huo, Suzhou (CN)

(73) Assignee: SUZHOU RAINMED MEDICAL TECHNOLOGY CO., LTD., Suzhou (CN)

(*) Notice: Subject to any disclaimer, the term of this patent is extended or adjusted under 35 U.S.C. 154(b) by 332 days.

(21) Appl. No.: 15/756,610

(22) PCT Filed: Dec. 3, 2015

(86) PCT No.: PCT/CN2015/096317
§ 371 (c)(1),
(2) Date: Mar. 1, 2018

(87) PCT Pub. No.: WO2017/041368
PCT Pub. Date: Mar. 16, 2017

(65) Prior Publication Data
US 2019/0110695 A1    Apr. 18, 2019

(30) Foreign Application Priority Data
Sep. 9, 2015 (CN) .......................... 201510570247.1

(51) Int. Cl.
*A61B 5/02* (2006.01)
*A61M 25/01* (2006.01)
(Continued)

(52) U.S. Cl.
CPC .......... *A61B 5/02007* (2013.01); *A61B 5/027* (2013.01); *A61B 5/6852* (2013.01); *A61M 25/01* (2013.01); *A61B 2505/05* (2013.01)

(58) Field of Classification Search
None
See application file for complete search history.

(56) References Cited

U.S. PATENT DOCUMENTS 4,840,182 A    6/1989 Carlson
7,454,244 B2   11/2008 Kassab et al.
(Continued)

FOREIGN PATENT DOCUMENTS

CN    102939051 A    2/2013
CN    103732132 A    4/2014
(Continued)

*Primary Examiner* — Matthew Kremer
*Assistant Examiner* — Aurelie H Tu
(74) *Attorney, Agent, or Firm* — SZDC Law P.C.

(57) ABSTRACT

A coronary artery load detection method includes: (S1) obtaining the cross-sectional area of a reference cavity, and separately obtaining voltage values of a primary device at a location corresponding to the cross-sectional area of the reference cavity in a low frequency state and a high frequency state; (S2) separately obtaining voltage values of the primary device at the location of a bottom end or a top end of a to-be-detected object in the low frequency state and the high frequency state under the same current; (S3) driving the primary device to move at a constant speed, and obtaining a voltage value of the primary device during the movement in the low frequency state under the same current; and (S4) obtaining the cross-sectional area of each location of the to-be-detected object according to a preset fixed current value, the cross-sectional area of the cavity, and the obtained voltage values.

12 Claims, 4 Drawing Sheets

(51) Int. Cl.
*A61B 5/00* (2006.01)
*A61B 5/027* (2006.01)

(56) References Cited

U.S. PATENT DOCUMENTS

| | | | |
|---|---|---|---|
| 2004/0230131 A1* | 11/2004 | Kassab | A61B 5/1076 600/547 |
| 2008/0294041 A1 | 11/2008 | Kassab | |
| 2011/0196255 A1 | 8/2011 | Kassab | |
| 2013/0060133 A1* | 3/2013 | Kassab | A61B 6/5217 600/431 |
| 2013/0184553 A1 | 7/2013 | Kassab et al. | |
| 2014/0378850 A1* | 12/2014 | Plakas | A61B 5/7275 600/504 |
| 2015/0025398 A1 | 1/2015 | Davies et al. | |
| 2015/0374243 A1* | 12/2015 | Itu | G06F 17/10 703/2 |

FOREIGN PATENT DOCUMENTS

| | | | |
|---|---|---|---|
| CN | 103874456 A | 6/2014 | |
| CN | 105078425 A | 11/2015 | |
| WO | 9835611 A1 | 8/1998 | |
| WO | 2011085210 A1 | 7/2011 | |
| WO | 2011159621 A2 | 12/2011 | |

* cited by examiner

CORONARY ARTERY LOAD DETECTING SYSTEM AND METHOD

CROSS-REFERENCE TO RELATED APPLICATIONS

This application claims priority to Chinese Patent Application No. 201510570247.1, filed on Sep. 9, 2015, and entitled "CORONARY ARTERY LOAD DETECTION SYSTEM AND METHOD," which is incorporated herein by reference in its entirety.

TECHNICAL FIELD

The present invention belongs to the technical field of medical detection, and relates to a coronary artery load detection system and method.

BACKGROUND

With the rapid development of biomedical engineering, how to improve the early prevention to and treatment of diseases for the mankind, strengthen the body function and improve the health level has become a problem of common concern. Correspondingly, people have an increasingly higher requirement on medical detection means, and the detection methods have developed from manual detection to detection in cooperation with automatic devices. In the prior art, a single-form imaging diagnostic instrument is used in detection, which however cannot meet the requirement in early diagnosis of diseases. A new-type detection system that combines the form and the function is the trend of medical development. Development towards functionality check and early diagnosis of diseases, development and extension towards recovery from diseases, and evaluation after the recovery are the objectives pursued during the development of modern medicine.

Currently, the cardiovascular disease is a disease that the largest number of patients suffers, and has a highest mortality rate. In the prior art, during the coronary artery load detection, detection is usually performed by using such methods as CT and ultrasonic waves, and the stenosis rate of a blood vessel is directly obtained by using such devices. In this way, detection costs are high and the precision of an obtained detection result is relatively low. In addition, the foregoing devices can only analyze the stenosis rate of the blood vessel, but is under-diagnosed in information such as diffuse plaques (the main cause to acute myocardial infarction) and an FFR (reflecting the pumping capability of the heart).

SUMMARY

An objective of the present invention is to provide a coronary artery load detection system and method, and the method includes:

To achieve one objective of the invention, an implementation of the present invention provides a coronary artery load detection method, and the method includes: S1. obtaining the cross-sectional area of a reference cavity, and separately obtaining voltage values of a primary device at a location corresponding to the cross-sectional area of the reference cavity in a low frequency state and a high frequency state;

S2. separately obtaining voltage values of the primary device at the location of a bottom end of a to-be-detected object in the low frequency state and the high frequency state under the same current;

S3. driving the primary device to move at a constant speed, and obtaining a voltage value of the primary device during the movement in the low frequency state under the same current; and S4. obtaining the cross-sectional area of each location of the to-be-detected object according to a preset fixed current value, the cross-sectional area of the reference cavity, and the voltage values obtained by means of the steps S1, S2 and S3.

To achieve one objective of the invention, an implementation of the present invention provides a coronary artery load detection system, and the system includes: a control module, a data collection module, and a data processing module;

the data collection module is configured to: obtain the cross-sectional area of a reference cavity, and separately obtain voltage values of a primary device at a location corresponding to the cross-sectional area of the reference cavity in a low frequency state and a high frequency state; and separately obtain voltage values of the primary device at the location of a bottom end of a to-be-detected object in the low frequency state and the high frequency state under the same current;

the control module is configured to drive the primary device to move at a constant speed, and the data collection module is further configured to: obtain a voltage value of the primary device during the movement in the low frequency state under the same current; and the data processing module is configured to obtain the cross-sectional area of each location of the to-be-detected object according to a preset fixed current value, the cross-sectional area of the cavity, and the obtained voltage values.

Compared with the prior art, the beneficial effects of the present invention are: According to the coronary artery load detection system and method of the present invention, a voltage value of each location of a to-be-detected object is obtained in a frequency conversion mode, so that the sectional area of each location of the to-be-detected object is obtained by means of parsing. Further, during parsing of the voltage value, an optimum voltage value of a known loop can be obtained by performing linear interpolation on a voltage value across two end of the loop, and an impact of a plaque existing in a blood vessel on the parsing result is eliminated. Still further, the sectional area of each location of the to-be-detected object is parsed, to obtain the diameter stenosis, a plaque parameter, and a fractional flow reserve FFR of each location of the to-be-detected object. During implementation of the method, provided that an impedance catheter is retraced at a constant speed for only one time, the sectional area of each location in the blood vessel can be precisely learned of, and the diameter stenosis of each location is further obtained, thereby greatly simplifying an operating and processing process and reducing the detection costs.

DETAILED DESCRIPTION OF PREFERRED EMBODIMENTS

The following describes the present invention in detail with reference to the implementations shown in the accompanying drawings. However, the implementations are not intended to limit the present invention. All variations made on the structure, method, or function by a person of ordinary skill in the art according to the implementations shall fall within the protection scope of the present invention.

Figure 1:
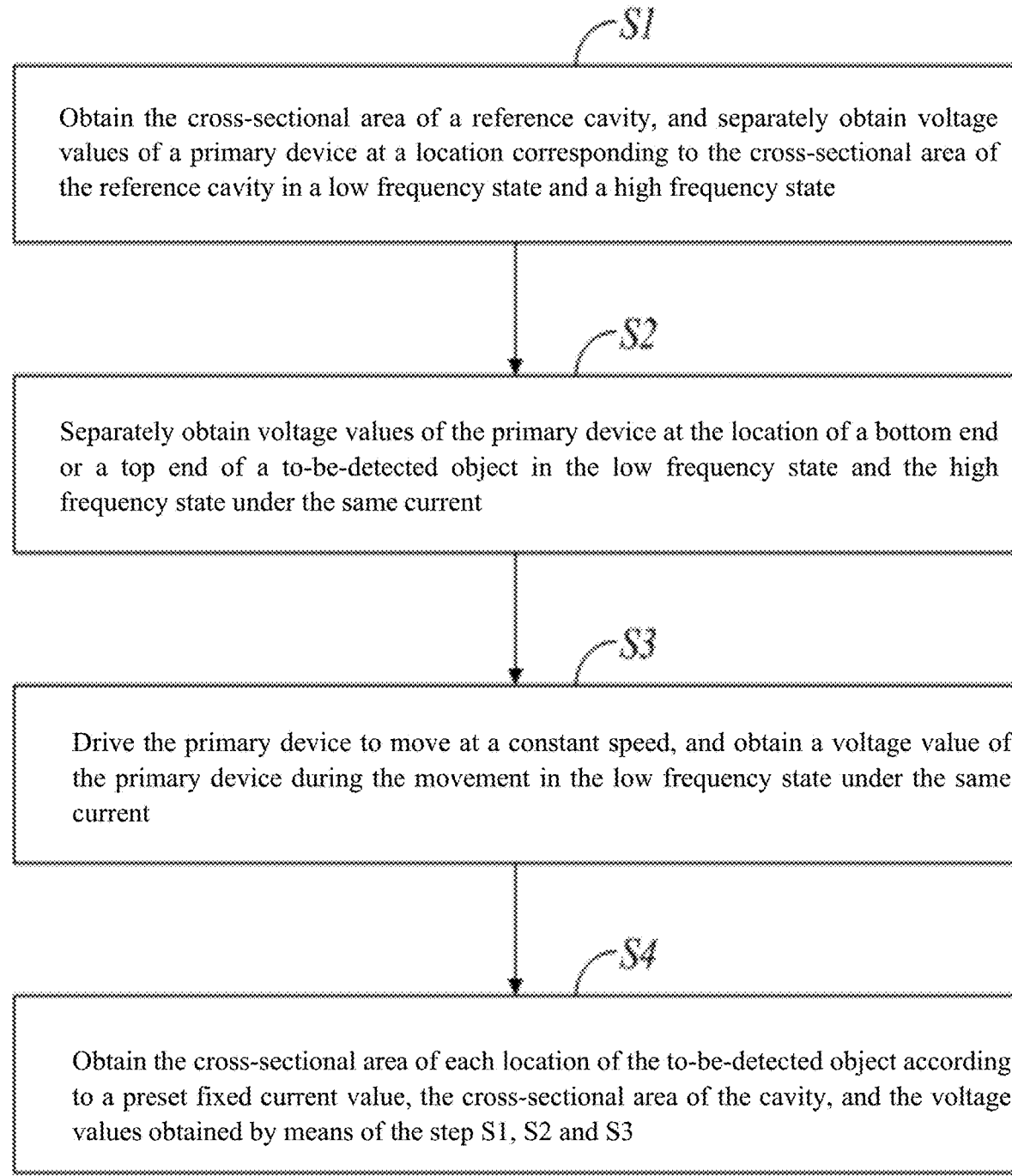
FIG. 1 is a schematic flowchart of a coronary artery load detection method according to an implementation of the present invention.

As shown in FIG. 1, an implementation of the present invention provides a coronary artery load detection method, and the method includes:

S1. Obtain the cross-sectional area of a reference cavity, and separately obtain voltage values of a primary device at a location corresponding to the cross-sectional area of the reference cavity in a low frequency state and a high frequency state.

In this implementation, the cross-sectional area of the reference cavity is the cross-sectional area of a sheath through which the primary device reaches a to-be-detected object during detection, the to-be-detected object is a blood vessel, and the primary device is an impedance catheter. Correspondingly, voltage values of the impedance catheter at the location of a bottom end of the sheath are separately obtained in the low frequency state and the high frequency state under the same current under the same current.

It should be noted that for ease of description, in the following examples, during application of the impedance catheter, an end of the impedance catheter near an operator is defined as a near end, and an end of the impedance catheter away from the operator is defined as a far end.

Figure 5:
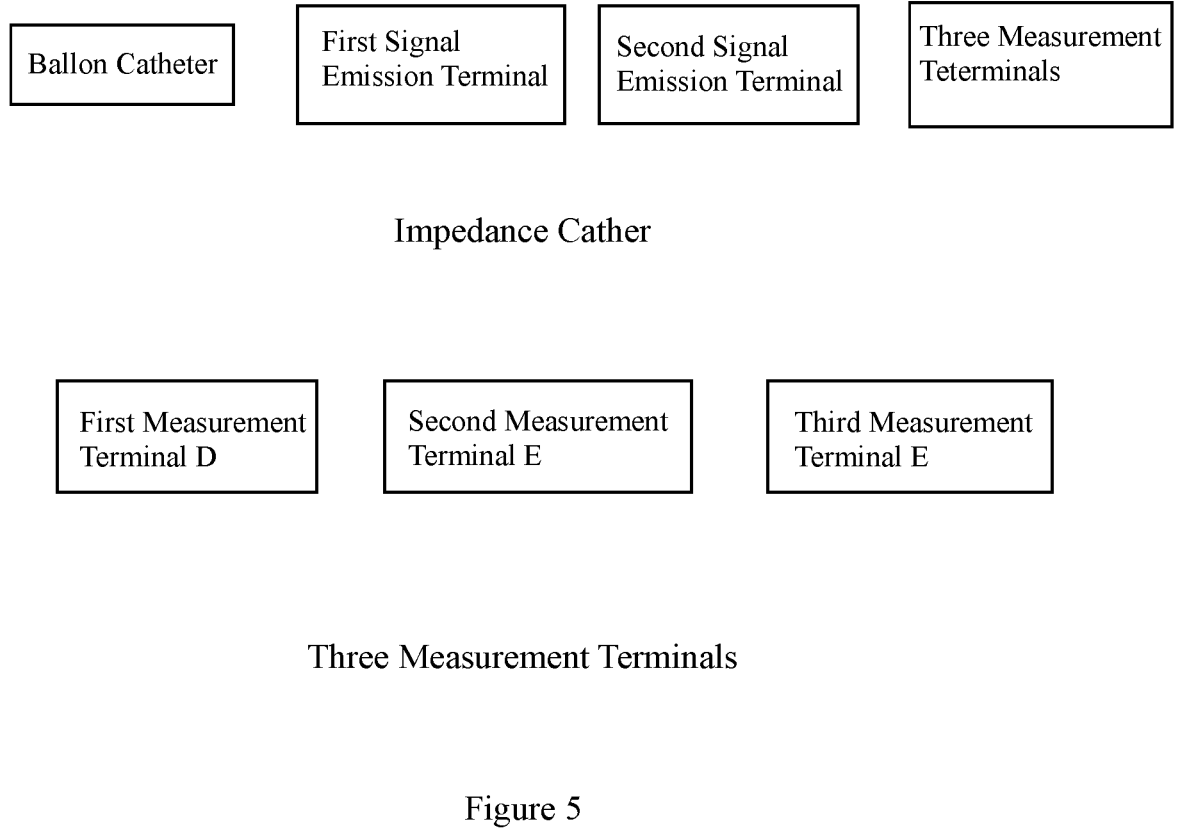
FIG. 5 shows an impedance catheter that includes a balloon catheter, a first signal emission terminal, a second signal emission terminal, and three measurement terminals and that the measurement terminals include a first measurement terminal D, a second measurement terminal E and a third measurement terminal F.

As shown in FIG. 5, the impedance catheter includes: a balloon catheter, a first signal emission terminal disposed at a far end of the balloon catheter, a second signal emission terminal disposed at a near end of the balloon catheter, and at least three measurement terminals that are equally spaced and that are disposed between the first signal emission terminal and the second signal emission terminal on the balloon catheter and have the same size and performance, each two of the measurement terminals forming a loop with the first signal emission terminal and the second signal emission terminal. In this way, the density of generated currents are relatively evenly distributed, and when signal extraction is performed by using a voltage-type operational amplifier with high input impedance in a later stage, the impact of the measurement terminals on a liquid in the blood vessel, which may be considered as an electrolyte, may be neglected.

There are three measurement terminals, and the measurement terminals include: a first measurement terminal D, a second measurement terminal E and a third measurement terminal F that are sequentially disposed from a location near the first signal emission terminal to the second signal emission terminal, where the distance between the first measurement terminal D and the second measurement terminal E is equal to the distance between the second measurement terminal E and the third measurement terminal F.

A D-E loop is formed between the first measurement terminal D and the second measurement terminal E, an E-F loop is formed between the second measurement terminal E and the third measurement terminal F, and a D-F loop is formed between the first measurement terminal D and the third measurement terminal F.

The voltage values include: a first voltage value corresponding to the D-E loop, a second voltage value corresponding to the D-F loop, and a third voltage value corresponding to the E-F loop.

In a specific example of the present invention, a first micro-signal generation terminal and a second micro-signal generation terminal generate micro-currents having a size of 5 microamperes to 20 microamperes and a frequency of 5 KHz to 200 KHz. In addition, during the whole measurement, currents of the same size are emitted, to ensure that a precise measurement result is obtained.

The widths of the first micro-signal generation terminal and the second micro-signal generation terminal and the measurement terminals all may be 0.5 mm to 1.5 mm. The measurement terminals are all equally spaced by 0.5 mm to 2 mm.

In a preferred example of the present invention, the widths of the first micro-signal generation terminal and the second micro-signal generation terminal and the measurement terminals are all 1 mm, and the measurement terminals are all equally spaced by 1 mm.

In a specific example of the present invention, the impedance catheter extends into the to-be-detected object by means of the sheath. When the impedance catheter is located at the bottom end of the sheath, a first voltage value, a second voltage value, and a third voltage value of a current location are separately obtained in the low frequency state and the high frequency state.

In other implementations of the present invention, a super-smooth layer of a hydrophilic material is added to the outer wall surface of the impedance catheter to increase the reliability of in-body measurement, and no details are described herein.

Further, the coronary artery load detection method of the present invention further includes:

S2. Separately obtain voltage values of the primary device at the location of a bottom end or a top end of the to-be-detected object in the low frequency state and the high frequency state under the same current.

In a specific example of the present invention, the impedance catheter inserts into the location of the bottom end of the to-be-detected object, and the first voltage value, the second voltage value, and the third voltage value of the current location are separately obtained in the low frequency state and the high frequency state.

It may be understood that the values of the low frequency and the high frequency are not specifically limited, and the low frequency and the high frequency are only frequency bands relative to each other. For example, the low frequency is 5 KHZ and the relatively high frequency is 200 KHZ.

Further, the coronary artery load detection method of the present invention further includes:

S3. Drive the primary device to move at a constant speed, and obtain a voltage value of the primary device during the movement in the low frequency state under the same current.

In an implementation of the present invention, a first voltage value, a second voltage value, and a third voltage value corresponding to each location of the to-be-detected object are obtained during the movement of the impedance catheter only in the low frequency state.

In other implementations of the present invention, referring to step S2, a first voltage value, a second voltage value, and a third voltage value corresponding to each location of the to-be-detected object are obtained during the movement of the impedance catheter in the low frequency state and the high frequency state.

The foregoing two implementations are separately described in below content.

Further, the coronary artery load detection method of the present invention further includes:

S4. Obtain the cross-sectional area of each location of the to-be-detected object according to a preset fixed current value, the cross-sectional area of the cavity, and the voltage values obtained by means of the steps S1, S2 and S3.

During specific implementation of the present invention, the preset fixed current value is a value of a current emitted by each of the first measurement terminal and the second measurement terminal, and the value of the current may be arbitrarily adjusted according to an actual requirement. However, it should be noted that the value of the current always retains unchanged during the entire measurement, and no details are described herein.

The step S4 specifically includes:

P1. Process the voltage values obtained by means of the step S1 and the cross-sectional area of the reference cavity, to obtain a constant C by dividing the electrical conductivity of a liquid flowing in the to-be-detected object by an effective length between two corresponding measurement terminals.

The following are obtained when the primary device is in the low frequency state:

$$C_1 = \frac{I}{U_1 \cdot \text{Area}_{IC}}, C_2 = \frac{I}{U_{12} \cdot \text{Area}_{IC}}, C_3 = \frac{I}{U_2 \cdot \text{Area}_{IC}},$$

In a specific example of the present invention, because the first measurement terminal D, the second measurement terminal E, and the third measurement terminal F are equally spaced, and the electrical conductivity of the liquid flowing in the to-be-detected object is fixed, the following is then obtained: $C_1 = C_2 = 2C_3$, where a constant $C_1$, a constant $C_2$, and a constant $C_3$ are respectively obtained by dividing the electrical conductivity of the liquid flowing in the to-be-detected object by an effective length between two corresponding measurement terminals when the impedance catheter is in the to-be-detected object in the low frequency state, and $\text{Area}_{IC}$ represents the cross-sectional area of the reference cavity. In this example, $\text{Area}_{IC}$ represents the cross-sectional area of the cavity of the sheath, and the value of $\text{Area}_{IC}$ may be determined at delivery of the sheath. $U_1$ represents the first voltage value, $U_2$ represents the second voltage value, $U_{12}$ represents the third voltage value, both $U_1$ and $U_2$ are directly obtained by using the impedance catheter, and $U_{12}$ is calculated by using $U_1$ and $U_2$, where $U_{12} = U_2 - U_1$. I is the preset fixed current value, and in this example, represents the size of the current emitted by each of the first signal emission terminal and the second signal emission terminal.

Similarly, the following are obtained when the primary device is in the high frequency state:

$$C'_1 = \frac{I}{U'_1 \cdot \text{Area}_{IC}}, C'_2 = \frac{I}{U'_{12} \cdot \text{Area}_{IC}}, C'_3 = \frac{I}{U'_2 \cdot \text{Area}_{IC}},$$

$$C'_1 = C'_2 = 2C'_3,$$

where a constant $C'_1$, a constant $C'_2$, and a constant $C'_3$ are respectively obtained by dividing the electrical conductivity of the liquid flowing in the to-be-detected object by an effective length between two corresponding measurement terminals when the impedance catheter is in the to-be-detected object in the high frequency state, $\text{Area}_{IC}$ represents the cross-sectional area of the reference cavity, $U'_1$ represents the first voltage value, $U'_2$ represents the second voltage value, $U'_{12}$ represents the third voltage value, both $U'_1$ and $U'_2$ are directly obtained using the impedance catheter, and $U'_{12}$ is calculated by using $U'_1$ and $U'_2$, where $U'_{12} = U'_2 - U'_1$.

The step S4 further includes:

P2. Obtain, according to the constant C obtained after the step P1 and the voltage values obtained by means of the step S2, the sectional area of the to-be-detected object when the impedance catheter is located at the bottom end of the to-be-detected object.

The following is obtained when the primary device is in the low frequency state:

$$\frac{I}{U_{1_{t=0}}} - \text{Area}_{t=0} \cdot C_1 = K_{1_{t=0}}; \text{ or}$$

the following is obtained when the primary device is in the high frequency state:

$$\frac{I}{U'_{1_{t=0}}} - \text{Area}_{t=0} \cdot C'_1 = K'_{1_{t=0}};$$

so that when the impedance catheter is located at the bottom end of the to-be-detected object, the sectional area of the to-be-detected object is:

$$\text{Area}_{t=0} = \left( \frac{I}{U'_{1_{t=0}}} - \frac{I}{U_{1_{t=0}}} \right) \Big/ (C'_1 - C_1),$$

where $K_{1_{t=0}}$ represents the electrical conductivity of the to-be-detected object, $\text{Area}_{t=0}$ represents the sectional area of the to-be-detected object when the impedance catheter is located at the bottom end of the to-be-detected object, $U_{1_{t=0}}$ represents the first voltage value when the impedance catheter is located at the bottom end of the to-be-detected object at a low frequency, and $U'_{1_{t=0}}$ represents the first voltage value when the impedance catheter is located at the bottom end of the to-be-detected object at a high frequency.

In an implementation of the present invention, after the step P2, the step S4 further includes:

P31. Drive the impedance catheter to retrace at a constant speed. During the retracement of the impedance catheter, at a time point $t = n \cdot \Delta t$, where n is a constant whose value is a positive integer greater than 0, a distance difference between a current location of the impedance catheter and the location of the bottom end of the to-be-detected object at which the impedance catheter is located is: $L = V \cdot n \cdot \Delta t$, where V represents a retracement speed of the impedance catheter. For ease of description, the voltage values obtained during the retracement of the impedance catheter are represented according to a time-varying rule. That is, under the low frequency state, when the first voltage value is represented as $U_{1_{t=0}}$ when the impedance catheter is located at the bottom end of the to-be-detected object, a measured first voltage value may be represented as $U_{1_{t=n}}$ during the movement of the impedance catheter at a constant speed. Correspondingly, the second voltage value may be represented as $U_{2_{t=n}}$, and the third voltage value may be represented as $U_{3_{t=n}}$.

In a preferred implementation of the present invention, the step P31 specifically includes: performing linear interpolation on the sectional area $Area_{t=(n-1) \cdot \Delta t}$ of a to-be-detected object corresponding to the D-E loop and the sectional area $Area_{t=n \cdot \Delta t}$ of a to-be-detected object corresponding to the E-F loop, to obtain the sectional area of a to-be-detected object corresponding to the D-F loop:

$$\frac{Area_{t=(n-1) \cdot \Delta t} \cdot C_1 + Area_{t=n \cdot \Delta t} \cdot C_2}{C_1 + C_2}$$

In this way, when the to-be-detected object is a blood vessel, an impact of a plaque existing in the blood vessel on a parsing result is eliminated.

At the time point t, the following are obtained when the primary device is in the low frequency state:

$$\frac{I}{U_{1_{t=n}}} - Area_{t=(n-1) \cdot \Delta t} \cdot C_1 = K_{1_{t=n \cdot \Delta t}},$$

$$\frac{I}{U_{12_{t=n}}} - Area_{t=n \cdot \Delta t} \cdot C_2 = K_{2_{t=n \cdot \Delta t}},$$

$$\frac{I}{U_{2_{t=n}}} - \frac{Area_{t=(n-1) \cdot \Delta t} \cdot C_1 + Area_{t=n \cdot \Delta t} \cdot C_2}{C_1 + C_2} \cdot C_3 = \frac{1}{\frac{1}{K_{1_{t=n \cdot \Delta t}}} + \frac{1}{K_{2_{t=n \cdot \Delta t}}}},$$

the following can be obtained upon introducing $C_1 = C_2 = 2C_3$:

$$\frac{I}{U_{1_{t=n}}} - Area_{t=(n-1) \cdot \Delta t} \cdot 2C_3 = K_{1_{t=n \cdot \Delta t}},$$

$$\frac{I}{U_{12_{t=n}}} - Area_{t=n \cdot \Delta t} \cdot 2C_3 = K_{2_{t=n \cdot \Delta t}},$$

$$\frac{I}{U_{2_{t=n}}} - \frac{Area_{t=(n-1) \cdot \Delta t} + Area_{t=n \cdot \Delta t}}{2} \cdot C_3 = \frac{1}{\frac{1}{K_{1_{t=n \cdot \Delta t}}} + \frac{1}{K_{2_{t=n \cdot \Delta t}}}},$$

The foregoing formulas are merged to eliminate $K_{1_{t=n \cdot \Delta t}}$ and $K_{2_{t=n \cdot \Delta t}}$, and further eliminate the impact of the plaque existing in the blood vessel on the parsing result, so that:

$$C_3 \cdot (Area_{t=n \cdot \Delta t})^2 +$$

$$\left(\frac{3}{2} \cdot \frac{I}{U_{1_{t=n}}} - \frac{1}{2} \cdot \frac{I}{U_{12_{t=n}}} - 2 \cdot \frac{I}{U_{2_{t=n}}} - 2 \cdot C_3 \cdot Area_{t=(n-1) \cdot \Delta t}\right) \cdot Area_{t=n \cdot \Delta t} +$$

$$\left(\frac{3}{2} \cdot \frac{I}{U_{12_{t=n}}} - \frac{1}{2} \cdot \frac{I}{U_{1_{t=n}}} - 2 \cdot \frac{I}{U_{2_{t=n}}} + C_3 \cdot Area_{t=(n-1) \cdot \Delta t}\right) \cdot$$

$$Area_{t=(n-1) \cdot \Delta t} = 0,$$

For ease of description, defining:

$$B_3 = \left(\frac{3}{2} \cdot \frac{I}{U_{1_{t=n}}} - \frac{1}{2} \cdot \frac{I}{U_{12_{t=n}}} - 2 \cdot \frac{I}{U_{2_{t=n}}} - 2 \cdot C_3 \cdot Area_{t=(n-1) \cdot \Delta t}\right),$$

$$A_3 = \left(\frac{3}{2} \cdot \frac{I}{U_{12_{t=n}}} - \frac{1}{2} \cdot \frac{I}{U_{1_{t=n}}} - 2 \cdot \frac{I}{U_{2_{t=n}}} + C_3 \cdot Area_{t=(n-1) \cdot \Delta t}\right) \cdot Area_{t=(n-1) \cdot \Delta t},$$

when the value of $$\frac{I}{U_{12_{t=n}}}$$

gradually increases, the cross-sectional area of each location of the to-be-detected object is:

$$Area_{t=n \cdot \Delta t} = \frac{-B_3 + \sqrt{B_3^2 - 4 \cdot C_3 \cdot A_3}}{2 \cdot C_3},$$

or
when the value of $$\frac{I}{U_{12_{t=n}}}$$

gradually decreases, the cross-sectional area of each location of the to-be-detected object is:

$$Area_{t=n \cdot \Delta t} = \frac{-B_3 - \sqrt{B_3^2 - 4 \cdot C_3 \cdot A_3}}{2 \cdot C_3},$$

where $Area_{t=n \cdot \Delta t}$ represents the cross-sectional area of each location of the to-be-detected object at a moment t, $K_{1_{t=n \cdot \Delta t}}$ represents the electrical conductivity of the to-be-detected object corresponding to the D-E loop at the moment t, $K_{2_{t=n \cdot \Delta t}}$ represents the electrical conductivity of the to-be-detected object corresponding to the E-F loop at the moment t, $U_{1_{t=n}}$ represents the first voltage value of the to-be-detected object corresponding to the D-E loop at the moment t, $U_{2_{t=n}}$ represents the second voltage value of the to-be-detected object corresponding to the E-F loop at the moment t, and $U_{12_{t=n}}$ represents the third voltage value of the to-be-detected object corresponding to the E-F loop at the moment t.

In another implementation of the present invention, after the step P2, the step P31 of obtaining the sectional area of each location of the to-be-detected object is replaced with P32.

That is, in another implementation of the present invention, the step S4 further includes:

P32. Obtain, according to the constant C obtained by means of step P2 and the voltage values obtained by means of the step S2 and step S3, the sectional area of each location of the to-be-detected object. In the step S3, the voltage value during the movement of the primary device further needs to be obtained in the high frequency state.

Therefore, the following is obtained when the primary device is in the low frequency state:

$$\frac{I}{U_{1_{t=n}}} - \text{Area}_{t=n} \cdot C_1 = K_{1_{t=n}};$$

or the following is obtained when the primary device is in the high frequency state:

$$\frac{I}{U'_{1_{t=n}}} - \text{Area}_{t=n} \cdot C'_1 = K_{1_{t=n}};$$

so that during the driving of the impedance catheter, when the impedance catheter is located at the bottom end of the to-be-detected object, the sectional area of the to-be-detected object is:

$$\text{Area}_{t=n} = \left(\frac{I}{U'_{1_{t=n}}} - \frac{I}{U_{1_{t=n}}}\right) \bigg/ (C'_1 - C_1),$$

where $K_{1_{t=0}}$ represents the electrical conductivity of the to-be-detected object, $\text{Area}_{t=0}$ represents the sectional area of the to-be-detected object when the impedance catheter is located at the bottom end of the to-be-detected object, $U_{1_{t=0}}$ represents the first voltage value when the impedance catheter is located at the bottom end of the to-be-detected object at a low frequency, and $U'_{1_{t=0}}$ represents the first voltage value when the impedance catheter is located at the bottom end of the to-be-detected object at a high frequency.

It should be noted that during the obtaining of the sectional area of each location of the to-be-detected object, noise processing may further be performed on transmission data, and the transmission data is the voltage value, current value and the like that are directly obtained by the impedance catheter. A noise processing process is for example: using a high impedance signal source, and using an operational amplifier that has low temperature drift with a low noise voltage and a low noise current and has a wide band and high impedance as a pre-amplifier. Similarly, during an alternating constant current source conversion, a device having a similar function may be selected. Further, since detection is for weak signals whose signal-to-noise ratio is relatively low, in addition to that an analog circuit is elaborately deployed to extract a signal, denoising may further be performed on the signals by using an FFT algorithm, to resolve the problem of low signal-to-noise ratio. Therefore, not only hardware circuit costs are reduced, but also real-time stability of a detection system is ensured.

Further, after the step S4, at least one of the diameter stenosis, a plaque parameter, and a fractional flow reserve FFR of each location of the to-be-detected object may further be obtained by parsing the sectional area obtained by means of the step S4. Further, a model of the to-be-detected object may further be drawn by obtaining the sectional area and the plaque parameter of each location of the to-be-detected object.

In an implementation of the present invention, after the step S4, the method may include:

S51. Obtain the diameter stenosis of each location of the to-be-detected object according to the cross-sectional area of each location of the to-be-detected object obtained by means of the step S4.

The sectional diameter of each location of the to-be-detected object is obtained according to the cross-sectional area of each location of the to-be-detected object, so that the stenosis rate of each location of the to-be-detected object is obtained.

The sectional diameter of each location of the to-be-detected object is $$D_{t=n} = \sqrt[2]{\frac{\text{Area}_{t=n} \times 4}{\pi}}.$$

Further, the diameter stenosis=(the sectional diameter of a normal location at an entrance of the to-be-detected object−the sectional diameter of a current location of the to-be-detected object)/the sectional diameter of the normal location at the entrance of the to-be-detected object*100%.

It may be understood that the diameter stenosis of the current location of the blood vessel determined in this implementation is obtained when the impedance catheter is located at the bottom end of the blood vessel. Therefore, when the to-be-detected object is a blood vessel, the impedance catheter inserts as much as possible to a location where the blood vessel is in a normal state, and no details are described herein.

In conclusion, according to the coronary artery load detection method of the present invention, a voltage value of each location of a to-be-detected object is obtained in a frequency conversion mode, so that the sectional area of each location of the to-be-detected object is obtained by means of parsing. Further, during parsing of the voltage values, an optimum voltage value of a known loop can be obtained by performing linear interpolation on a voltage value across two end of the loop, and an impact of a plaque existing in a blood vessel on a parsing result is eliminated. Still further, the sectional area of each location of the to-be-detected object is parsed, to obtain the diameter stenosis of each location of the to-be-detected object. During implementation of the method, provided that an impedance catheter is retraced at a constant speed for only one time, the sectional area of each location in the blood vessel can be precisely learned of, and the diameter stenosis of each location is further obtained. Different from the conventional method of obtaining the diameter stenosis by injecting substances with different electrical conductivities or by measuring data by means of imageology, in the present invention, the voltage value is obtained by using an impedance catheter, and no other auxiliary tool is needed, thereby greatly simplifying an operation and processing process and reducing the detection costs.

In an implementation of the present invention, after the step S4, the method may further include:

S52. Obtain a plaque parameter of each location of the to-be-detected object according to the cross-sectional area of each location of the to-be-detected object obtained by means of the step S4, and the voltage values obtained when the impedance catheter is located at each location of the to-be-detected object, where the plaque parameter is $$K_{t=n \cdot \Delta t} = \frac{I}{U_{12_{t=n}}} - \text{Area}_{t=n \cdot \Delta t} \cdot C_2.$$

It may be learned of according to the foregoing formula that a smaller value of the parameter K indicates higher content of fat in the wall of the blood vessel.

Certainly, in other implementations of the present invention, the cross-sectional area of each location of the blood vessel may further be obtained by means of imageology, for example, any imageological method such as CT, MM, and radiography, and no details are described herein.

In this way, in this implementation, provided that the impedance catheter is retraced at a constant speed for only one time, the sectional area of each location in the blood vessel can be precisely learned of, and the plaque parameter of each location is further obtained, thereby greatly simplifying an operation and processing process and reducing the detection costs.

In an implementation of the present invention, after the step S4, the method may include:

S53. Obtain a fractional flow reserve FFR of each location of the to-be-detected object according to the cross-sectional area of each location of the to-be-detected object obtained by means of the step S4.

It may be understood that the cross-sectional area of each location of the to-be-detected object may also be obtained by means of imageology described in the step S52, for example, any imageological method such as CT, MRI, and radiography, and no details are described herein.

The step S53 specifically includes:

M1. Classify the to-be-detected object into two regions according to the obtained cross-sectional area of each location of the to-be-detected object, where the two regions are respectively a normal region and a stenosis region.

In an implementation of the present invention, corresponding locations of the to-be-detected object whose values of area stenosis are less than 50% are classified into the normal region, and other locations are defined as the stenosis region. Certainly, in other implementations of the present invention, a demarcation point or demarcation manner for the normal region and the stenosis region may be demarcated as required, and no details are described herein.

The area stenosis=(the sectional area of a normal location at an entrance of the to-be-detected object–a current sectional area)/the sectional area of the normal location at the entrance of the to-be-detected object*100%.

Further, to simplify a calculation process, two or more stenosis regions are considered as the same stenosis region. In this implementation, a region classification threshold is set, and the region classification threshold is a length value. Whether a distance value between two neighboring stenosis regions is less than the region classification threshold is determined. If so, the neighboring two stenosis regions are considered as the same stenosis region.

M2. Calculate a pressure gradient for each of the normal region and the stenosis region.

Integrals of the pressure gradient $\Delta P_{normal}$ for the normal region are calculated by using the Poiseuille formula.

The calculating a pressure gradient $\Delta P_{stenosis}$ for the stenosis region includes: performing virtual correction on a bending part of the to-be-detected object; and decomposing the to-be-detected object into a two-dimensional axial symmetric model according to the cross-sectional area of each location, to generate a structured grid. In this way, three-dimensional calculation of the stenosis region is converted to two-dimensional calculation of the stenosis region, so that a calculation speed is improved by thousands of times.

Figure 3:
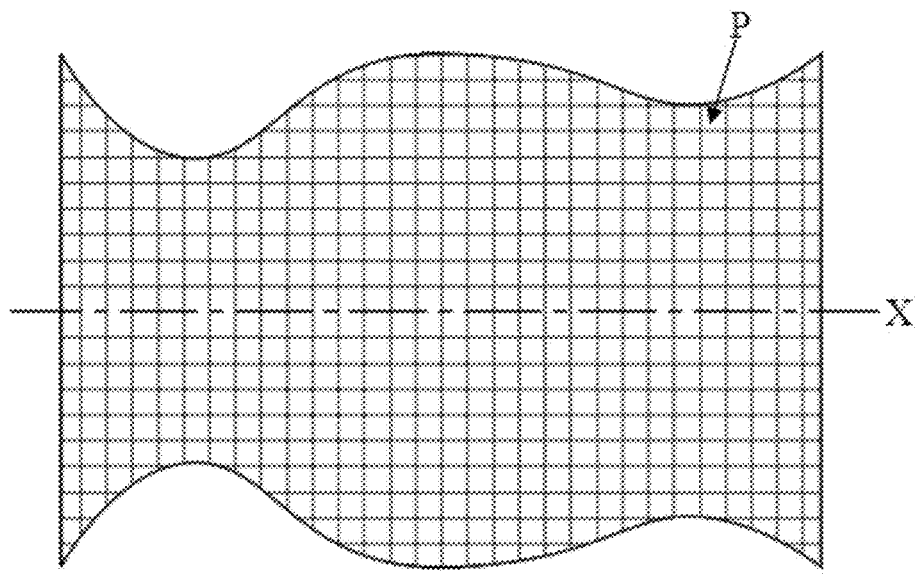
FIG. 3 is a schematic diagram of an axial symmetric structure obtained after a blood vessel is straightened according to a specific example according to the present invention.

With reference to FIG. 3, in a specific example of the present invention, the to-be-detected object is virtually straightened along an axial direction thereof, the straightened to-be-detected object is radially dissected to obtain a symmetric surface P, and the symmetric surface P is decomposed into two parts along its symmetric axis; and a two-dimensional symmetric model is generated according to the sectional area of each location of the to-be-detected object, then a structured grid is generated, and further, pressure gradient calculation is performed on the structured grid generated at either side of the symmetric axis.

In a specific example of the present invention, a contrast agent is injected for one time, and a reference speed of a blood flow in the blood vessel is precisely measured by using the impedance catheter. The reference speed is a normal flowing speed of the blood flow and is represented by $V_b$. A causative drug is injected for one time, and the blood flow speed is precisely measured by using the impedance catheter when the blood vessel is in a maximal congestion phase, and the blood flow speed in the maximal congestion phase is represented by $V_c$.

Certainly, the reference speed $V_b$ and the blood flow speed $V_c$ when the blood vessel is in the maximal congestion phase may also be obtained by using the radiography technology, and no details are described herein.

The equation of continuity and the momentum equation are solved by using the finite difference method according to the equation of continuity and the momentum equation in the theory of fluid mechanics, and the pressure gradient $\Delta P_{stenosis}$ of each location in the stenosis region is obtained.

In this implementation, according to the law of conservation of mass and the law of conservation of momentum, in the two-dimensional axial symmetric blood vessel, the pressure gradient is calculated by using the standard finite difference method, to solve the following equation:

$$\frac{1}{r}\frac{\partial}{\partial r}(ru_r) + \frac{\partial u_z}{\partial z} = 0,$$

$$\rho\left(\frac{\partial u_r}{\partial t} + u_r\frac{\partial u_r}{\partial r} + u_z\frac{\partial u_r}{\partial z}\right) = -\frac{\partial p}{\partial r} + \mu\left[\frac{1}{r}\frac{\partial}{\partial r}\left(r\frac{\partial u_r}{\partial r}\right) + \frac{\partial^2 u_r}{\partial z^2} - \frac{u_r}{r^2}\right],$$

$$\rho\left(\frac{\partial u_z}{\partial t} + u_r\frac{\partial u_z}{\partial r} + u_z\frac{\partial u_z}{\partial z}\right) = -\frac{\partial p}{\partial z} + \mu\left[\frac{1}{r}\frac{\partial}{\partial r}\left(r\frac{\partial u_z}{\partial r}\right) + \frac{\partial^2 u_z}{\partial z^2}\right],$$

where $\rho$ represents the density of blood, $u_z$ and $u_r$ respectively represent flowing speeds in the z direction and in the r direction, $\mu$ represents the kinetic viscosity of the blood, and p represents the intensity of pressure of the blood.

Further, the foregoing process may be corrected based on an angle impact parameter prestored in a backend database. In this way, the pressure gradient $P_{stenosis}$ through the stenosis region may be precisely calculated.

Further, the fractional flow reserve is obtained according to the obtained pressure gradient of the normal region and the stenosis region.

Upon introducing $\Delta P_{total} = \Sigma \Delta P_{normal} + \Sigma \Delta P_{stenosis}$, $$FFR = \frac{P_a - \Delta P_{total}}{P_a}$$

where FFR is the fractional flow reserve, $\Delta P_{total}$ is a sum of the pressure gradient of each location of the to-be-detected object, and $P_a$ is a constant. In this specific example, $P_a$ is the pressure of an aorta.

Further, whether a balloon dilation surgery needs to be carried out can be determined according to a value of the FFR. For example, when FFR>0.75, the balloon dilation surgery does not need to be carried out; or when FFR≤0.75, the balloon dilation surgery needs to be carried out. Certainly, the value demarcation point is only exemplary and may be adjusted as required during actual application, and no details are described herein.

According to the coronary artery load detection method of the present invention, conventional three-dimensional calculation is converted into two-dimensional model calculation. Further, rapid calculation is performed on the value of the two-dimensional axial symmetric model to parse out the pressure gradient of the stenosis region, so as to obtain the fractional flow reserve FFR of each location in the blood vessel. Meanwhile, in a process of converting the three-dimensional calculation into the two-dimensional calculation, virtual correction is further performed on the bending part of the blood vessel, thereby greatly simplifying a calculation process and improving the calculation efficiency. It may be known through tests that a calculation time is <30 s, ensuring rapid diagnosis of the FFR in a process of radiography and interventional surgery.

It may be understood that in a specific application example of the present invention, whether a balloon dilation surgery needs to be carried out can be further determined based on the parameters such as the stenosis location, the plaque load, and the FFR that are obtained above, and the balloon dilation surgery is precisely carried out, thereby greatly reducing risks of the interventional surgery.

An implementation of the present invention further provides a positioning method, and the method includes:

drawing a model of the to-be-detected object according to the obtained sectional area and the plaque parameter of each location of the to-be-detected object;

receiving a positioning instruction, where the positioning instruction is to determine a positioning target for this time by using the model of the to-be-detected object;

driving the primary device for the second time to the bottom end of the to-be-detected object, and retracing the primary device for the second time at a constant retracement speed the same as that used in the previous time; and stopping driving the primary device to move, when a parameter obtained by the primary device at the second time is the same as the positioning instruction.

In a specific application example of the present invention, if a current stopping location of the primary device is a stenosis location of the blood vessel, signals may be transmitted to a pressure pump (not shown). It should be noted that the pressure pump is also disposed in the impedance catheter, and the balloon dilation surgery is carried out by setting a pressure. In addition, a retracement action may further be performed on the impedance catheter once again to determine a dilation effect of a balloon on the blood vessel stenosis, and no details are described herein again.

In a specific example of the present invention, the sectional area and the plaque parameter of each location of the blood vessel are obtained according to the foregoing content to draw a model of the to-be-detected object, and the model is output to a display. A positioning target for this time is set, for example, a positioning instruction is input by using an external device such as a keyboard, or the positioning target for this time is positioned on the display by using an external device such as a mouse, to drive the impedance catheter for the second time to the bottom end of the to-be-detected object. The impedance catheter is retraced at a constant retracement speed the same as a speed used in the previous time, a measurement result of this time is output to the display according to the sectional area and the plaque parameter of each location of the blood vessel that are obtained by means of parsing. The measurement result of this time is compared with a measurement result of the previous time. If the impedance catheter reaches the location of the positioning target for this time, driving of the impedance catheter stops, and precise positioning is further performed.

Figure 2:
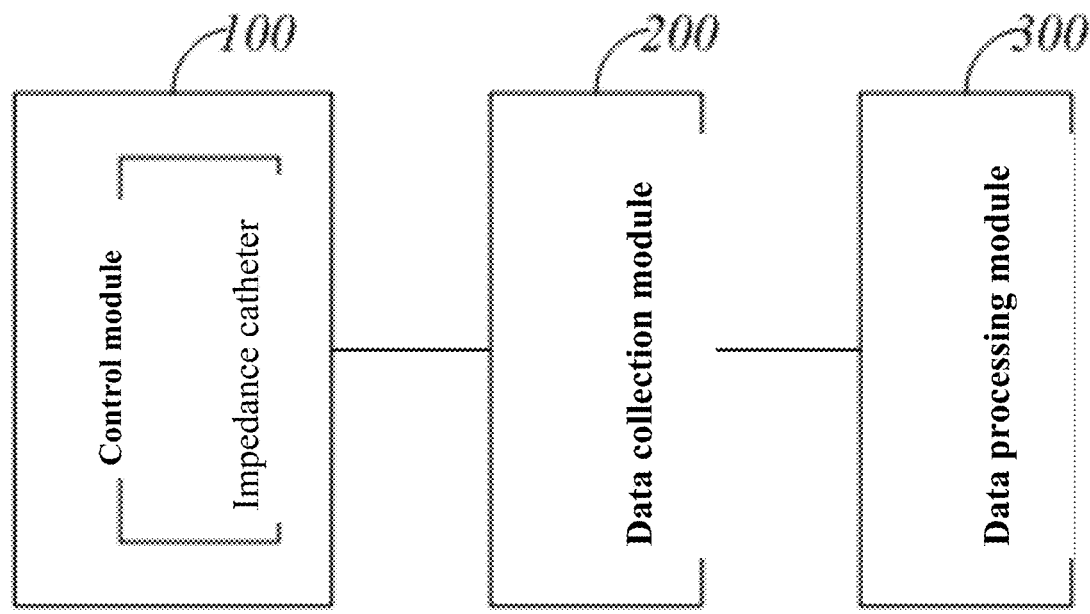
FIG. 2 is a schematic block diagram of a coronary artery load detection system according to an implementation of the present invention.

As shown in FIG. 2, an implementation of the present invention provides a coronary artery load detection system, and the system includes: a control module 100, a data collection module 200, and a data processing module 300.

The data collection module is configured to: obtain the cross-sectional area of a reference cavity, and separately obtain voltage values of a primary device at a location corresponding to the cross-sectional area of the reference cavity in a low frequency state and a high frequency state.

In this implementation, the cross-sectional area of the reference cavity is the cross-sectional area of a sheath through which the primary device passes to reach a to-be-detected object during detection, the to-be-detected object is a blood vessel, and the primary device is an impedance catheter. Correspondingly, the data collection module 100 separately obtains voltage values of the impedance catheter at the location of a bottom end of the sheath in the low frequency state and the high frequency state under the same current.

It should be noted that for ease of description, in the following examples, during application of the impedance catheter, an end of the impedance catheter near an operator is defined as a near end, and an end of the impedance catheter away from the operator is defined as a far end.

The impedance catheter includes: a balloon catheter, a first signal emission terminal disposed at a far end of the balloon catheter, a second signal emission terminal disposed at a near end of the balloon catheter, and at least three measurement terminals that are equally spaced and that are disposed between the first signal emission terminal and the second signal emission terminal on the balloon catheter and have the same size and performance, each two of the measurement terminals forming a loop with the first signal emission terminal and the second signal emission terminal. In this way, the density of generated currents are relatively evenly distributed, and when signal extraction is performed by using a voltage-type operational amplifier with high input impedance in a large stage, the impact of the measurement terminals on a liquid in the to-be-detected object, which may be considered as an electrolyte, may be neglected.

There are three measurement terminals, and the measurement terminals include: a first measurement terminal D, a second measurement terminal E and a third measurement terminal F that are sequentially disposed from a location near the first signal emission terminal to the second signal emission terminal, where the distance between the first measurement terminal D and the second measurement terminal E is equal to the distance between the second measurement terminal E and the third measurement terminal F.

A D-E loop is formed between the first measurement terminal D and the second measurement terminal E, an E-F loop is formed between the second measurement terminal E and the third measurement terminal F, and a D-F loop is formed between the first measurement terminal D and the third measurement terminal F.

The voltage values include: a first voltage value corresponding to the D-E loop, a second voltage value corresponding to the D-F loop, and a third voltage value corresponding to the E-F loop.

In a specific example of the present invention, a first micro-signal generation terminal and a second micro-signal generation terminal generate micro-currents having a size of 5 microamperes to 20 microamperes and a frequency of 5

KHz to 200 KHz. In addition, during the whole measurement, currents of the same size are emitted, to ensure that a precise measurement result is obtained.

The widths of the first micro-signal generation terminal and the second micro-signal generation terminal and the measurement terminals all may be 0.5 mm to 1.5 mm. The measurement terminals are all equally spaced by 0.5 mm to 2 mm.

In a preferred example of the present invention, the widths of the first micro-signal generation terminal and the second micro-signal generation terminal and the measurement terminals are all 1 mm, and the measurement terminals are all equally spaced by 1 mm.

In a specific example of the present invention, the control module 100 drives the impedance catheter to extend into the to-be-detected object by means of the sheath. When the impedance catheter is located at the bottom end of the sheath, the data collection module 200 separately obtains a first voltage value, a second voltage value, and a third voltage value of a current location in the low frequency state and the high frequency state. In other implementations of the present invention, a super-smooth layer of a hydrophilic material is added to the outer wall surface of the impedance catheter to increase the reliability of in-body measurement, and no details are described herein.

Further, the data collection module 200 is further configured to separately obtain voltage values of the primary device at the location of a bottom end or a top end of the to-be-detected object in the low frequency state and the high frequency state under the same current.

In a specific example of the present invention, the control module 100 drives the impedance catheter to insert into the location of the bottom end of the to-be-detected object, and the data collection module 200 separately obtains the first voltage value, the second voltage value, and the third voltage value of the current location in the low frequency state and the high frequency state.

It may be understood that the values of the low frequency and the high frequency are not specifically limited, and the low frequency and the high frequency are only frequency bands relative to each other. For example, the low frequency is 5 KHZ and the relatively high frequency is 200 KHZ.

Further, the control module 100 is further configured to drive the primary device to move at a constant speed, and the data collection module 200 obtains a voltage value of the primary device during the movement in the low frequency state under the same current.

In an implementation of the present invention, the data collection module 200 obtains a first voltage value, a second voltage value, and a third voltage value corresponding to each location of the to-be-detected object during the movement of the impedance catheter only in the low frequency state.

The data processing module 300 is configured to: obtain the cross-sectional areas of each location of the to-be-detected object according to a preset fixed current value, the cross-sectional area of the cavity, and the obtained voltage values.

During specific implementation of the present invention, the preset fixed current value is a value of a current emitted by each of the first measurement terminal and the second measurement terminal, and the value of the current may be arbitrarily adjusted according to an actual requirement. However, it should be noted that the value of the current always retains unchanged during the entire measurement, and no details are described herein.

The data processing module 300 is specifically configured to: process the obtained voltage values and the cross-sectional area of the reference cavity, to obtain a constant C by dividing the electrical conductivity of a liquid flowing in the to-be-detected object by an effective length between two corresponding measurement terminals.

The following are obtained when the primary device is in the low frequency state:

$$C_1 = \frac{I}{U_1 \cdot \text{Area}_{IC}}, C_2 = \frac{I}{U_{12} \cdot \text{Area}_{IC}}, C_3 = \frac{I}{U_2 \cdot \text{Area}_{IC}},$$

In a specific example of the present invention, because the first measurement terminal D, the second measurement terminal E, and the third measurement terminal F are equally spaced, and the electrical conductivity of the liquid flowing in the to-be-detected object is fixed, the following is then obtained: $C_1=C_2=2C_3$, where a constant $C_1$, a constant $C_2$, and a constant $C_3$ are respectively obtained by dividing the electrical conductivity of the liquid flowing in the to-be-detected object by an effective length between two corresponding measurement terminals when the impedance catheter is in the to-be-detected object in the low frequency state, and $\text{Area}_{IC}$ represents the cross-sectional area of the reference cavity. In this example, $\text{Area}_{IC}$ represents the cross-sectional area of the cavity of the sheath, and the value of $\text{Area}_{IC}$ may be determined at delivery of the sheath. $U_1$ represents the first voltage value, $U_2$ represents the second voltage value, $U_{12}$ represents the third voltage value, both $U_1$ and $U_2$ are directly obtained using the impedance catheter, and $U_{12}$ is calculated by using $U_1$ and $U_2$, where $U_{12}=U_2-U_1$. I is the preset fixed current value, and in this example, represents the size of the current emitted by each of the first signal emission terminal and the second signal emission terminal.

Similarly, the following are obtained when the primary device is in the high frequency state:

$$C'_1 = \frac{I}{U'_1 \cdot \text{Area}_{IC}}, C'_2 = \frac{I}{U'_{12} \cdot \text{Area}_{IC}}, C'_3 = \frac{I}{U'_2 \cdot \text{Area}_{IC}},$$

$$C'_1 = C'_2 = 2C'_3,$$

where a constant $C'_1$, a constant $C'_2$, and a constant $C'_3$ are respectively obtained by dividing the electrical conductivity of the liquid flowing in the to-be-detected object by an effective length between two corresponding measurement terminals when the impedance catheter is in the to-be-detected object in the high frequency state, $\text{Area}_{IC}$ represents the cross-sectional area of the reference cavity, $U'_1$ represents the first voltage value, $U'_2$ represents the second voltage value, $U'_{12}$ represents the third voltage value, both $U'_1$ and $U'_2$ are directly obtained by using the impedance catheter, and $U'_{12}$ is calculated by using $U'_1$ and $U'_2$, where $U'_{12}=U'_2-U'_1$.

The data processing module 300 is further configured to: obtain, according to the constant C obtained after the foregoing processing and the obtained voltage values, the sectional area of the to-be-detected object when the impedance catheter is located at the bottom end of the to-be-detected object.

The following are obtained when the primary device is in the low frequency state:

$$\frac{I}{U_{1_{t=0}}} - \text{Area}_{t=0} \cdot C_1 = K_{1_{t=0}};$$

or the following is obtained when the primary device is in the high frequency state:

$$\frac{I}{U'_{1_{t=0}}} - \text{Area}_{t=0} \cdot C'_1 = K_{1_{t=0}};$$

so that when the impedance catheter is located at the bottom end of the to-be-detected object, the sectional area of the to-be-detected object is:

$$\text{Area}_{t=0} = \left(\frac{I}{U'_{1_{t=0}}} - \frac{I}{U_{1_{t=0}}}\right) / (C'_1 - C_1),$$

where $K_{1_{t=0}}$ represents the electrical conductivity of the to-be-detected object, $\text{Area}_{t=0}$ represents the sectional area of the to-be-detected object when the impedance catheter is located at the bottom end of the to-be-detected object, $U_{1_{t=0}}$ represents the first voltage value when the impedance catheter is located at the bottom end of the to-be-detected object at a low frequency, and $U'_{1_{t=0}}$ represents the first voltage value when the impedance catheter is located at the bottom end of the to-be-detected object at a high frequency.

After the data processing module 300 obtains the sectional area of the to-be-detected object when the impedance catheter is located at the bottom end of the to-be-detected object, the data processing module 300 has two implementations according to the different voltage values obtained by the data processing module 300. In an implementation of the present invention, the control module 100 drives the impedance catheter to retrace at a constant speed. During the retracement of the impedance catheter, at a time point $t=n\cdot\Delta t$, where n is a constant whose value is a positive integer greater than 0, a distance difference between a current location of the impedance catheter and the location of the bottom end of the to-be-detected object at which the impedance catheter is located is: $L=V\cdot n\cdot\Delta t$, where V represents a retracement speed of the impedance catheter. For ease of description, the voltage values obtained during the retracement of the impedance catheter are represented according to a time-varying rule. That is, under the low frequency state, when the first voltage value is represented as $U_{1_{t=0}}$ when the impedance catheter is located at the bottom end of the to-be-detected object, a measured first voltage value may be represented as $U_{1_{t=n}}$ during the movement of the impedance catheter at a constant speed. Correspondingly, the second voltage value may be represented as $U_{2_{t=n}}$, and the third voltage value may be represented as $U_{3_{t=n}}$.

In this implementation, the data processing module 300 is specifically configured to: perform linear interpolation on the sectional area $\text{Area}_{t=(n-1)\cdot\Delta t}$ of a to-be-detected object corresponding to the D-E loop and the sectional area $\text{Area}_{t=n\cdot\Delta t}$ of a to-be-detected object corresponding to the E-F loop, to obtain the sectional area of a to-be-detected object corresponding to the D-F loop:

$$\frac{\text{Area}_{t=(n-1)\cdot\Delta t} \cdot C_1 + \text{Area}_{t=n\cdot\Delta t} \cdot C_2}{C_1 + C_2}$$

In this way, when the to-be-detected object is a blood vessel, an impact of a plaque existing in the blood vessel on a parsing result is eliminated.

At the time point t, the following are obtained when the primary device is in the low frequency state:

$$\frac{I}{U_{1_{t=n}}} - \text{Area}_{t=(n-1)\cdot\Delta t} \cdot C_1 = K_{1_{t=n\cdot\Delta t}},$$

$$\frac{I}{U_{12_{t=n}}} - \text{Area}_{t=n\cdot\Delta t} \cdot C_2 = K_{2_{t=n\cdot\Delta t}},$$

$$\frac{I}{U_{2_{t=n}}} - \frac{\text{Area}_{t=(n-1)\cdot\Delta t} \cdot C_1 + \text{Area}_{t=n\cdot\Delta t} \cdot C_2}{C_1 + C_2} \cdot C_3 = \frac{1}{\frac{1}{K_{1_{t=n\cdot\Delta t}}} + \frac{1}{K_{2_{t=n\cdot\Delta t}}}},$$

the following can be obtained upon introducing: $C_1 = C_2 = 2C_3$ $$\frac{I}{U_{1_{t=n}}} - \text{Area}_{t=(n-1)\cdot\Delta t} \cdot 2C_3 = K_{1_{t=n\cdot\Delta t}},$$

$$\frac{I}{U_{12_{t=n}}} - \text{Area}_{t=n\cdot\Delta t} \cdot 2C_3 = K_{2_{t=n\cdot\Delta t}},$$

$$\frac{I}{U_{2_{t=n}}} - \frac{\text{Area}_{t=(n-1)\cdot\Delta t} + \text{Area}_{t=n\cdot\Delta t}}{2} \cdot C_3 = \frac{1}{\frac{1}{K_{1_{t=n\cdot\Delta t}}} + \frac{1}{K_{2_{t=n\cdot\Delta t}}}}$$

The foregoing formulas are merged to eliminate $K_{1_{t=n\cdot\Delta t}}$ and $K_{2_{t=n\cdot\Delta t}}$, and further eliminate the impact of the plaque existing in the blood vessel on the parsing result, so that:

$$C_3 \cdot (\text{Area}_{t=n\cdot\Delta t})^2 +$$
$$\left(\frac{3}{2} \cdot \frac{I}{U_{1_{t=n}}} - \frac{1}{2} \cdot \frac{I}{U_{12_{t=n}}} - 2 \cdot \frac{I}{U_{2_{t=n}}} - 2 \cdot C_3 \cdot \text{Area}_{t=(n-1)\cdot\Delta t}\right) \cdot \text{Area}_{t=n\cdot\Delta t} +$$
$$\left(\frac{3}{2} \cdot \frac{I}{U_{12_{t=n}}} - \frac{1}{2} \cdot \frac{I}{U_{1_{t=n}}} - 2 \cdot \frac{I}{U_{2_{t=n}}} + C_3 \cdot \text{Area}_{t=(n-1)\cdot\Delta t}\right) \cdot$$
$$\text{Area}_{t=(n-1)\cdot\Delta t} = 0$$

For ease of description, defining:

$$B_3 = \left(\frac{3}{2} \cdot \frac{I}{U_{1_{t=n}}} - \frac{1}{2} \cdot \frac{I}{U_{12_{t=n}}} - 2 \cdot \frac{I}{U_{2_{t=n}}} - 2 \cdot C_3 \cdot \text{Area}_{t=(n-1)\cdot\Delta t}\right),$$

$$A_3 = \left(\frac{3}{2} \cdot \frac{I}{U_{12_{t=n}}} - \frac{1}{2} \cdot \frac{I}{U_{1_{t=n}}} - 2 \cdot \frac{I}{U_{2_{t=n}}} + C_3 \cdot \text{Area}_{t=(n-1)\cdot\Delta t}\right) \cdot \text{Area}_{t=(n-1)\cdot\Delta t};$$

when the value of $$\frac{I}{U_{12_{t=n}}}$$

gradually increases, the cross-sectional area of each location of the to-be-detected object is:

$$\text{Area}_{t=n\cdot\Delta t} = \frac{-B_3 + \sqrt{B_3^2 - 4\cdot C_3 \cdot A_3}}{2\cdot C_3},$$

or when the value of $$\frac{I}{U_{12_{t=n}}}$$

gradually decreases, the cross-sectional area of each location of the to-be-detected object is:

$$\text{Area}_{t=n\cdot\Delta t} = \frac{-B_3 - \sqrt{B_3^2 - 4\cdot C_3 \cdot A_3}}{2\cdot C_3},$$

where $\text{Area}_{t=n\cdot\Delta t}$ represents the cross-sectional area of each location of the to-be-detected object at a moment t, $K_{1_{t=n\cdot\Delta t}}$ represents the electrical conductivity of the to-be-detected object corresponding to the D-E loop at the moment t, $K_{2_{t=n\cdot\Delta t}}$ represents the electrical conductivity of the to-be-detected object corresponding to the E-F loop at the moment t, $U_{1_{t=n}}$ represents the first voltage value of the to-be-detected object corresponding to the D-E loop at the moment t, $U_{2_{t=n}}$ represents the second voltage value of the to-be-detected object corresponding to the E-F loop at the moment t, and $U_{12_{t=n}}$ represents the third voltage value of the to-be-detected object corresponding to the E-F loop at the moment t.

In another implementation of the present invention, the data collection module 200 is further configured to separately obtain the first voltage value, the second voltage value, and the third voltage value corresponding to each location of the to-be-detected object in the low frequency state and the high frequency state during the movement of the impedance catheter. In this case, the data processing module 300 is configured to obtain, according to the obtained constant C and the voltage values, the sectional area of each location of the to-be-detected object.

Therefore, the following is obtained when the primary device is in the low frequency state:

$$\frac{I}{U_{1_{t=n}}} - \text{Area}_{t=n} \cdot C_1 = K_{1_{t=n}};$$

or the following is obtained when the primary device is in the high frequency state:

$$\frac{I}{U'_{1_{t=n}}} - \text{Area}_{t=n} \cdot C'_1 = K_{1_{t=n}};$$

so that during the driving of the impedance catheter, when the impedance catheter is located at the bottom end of the to-be-detected object, the sectional area of the to-be-detected object is:

$$\text{Area}_{t=n} = \left(\frac{I}{U'_{1_{t=n}}} - \frac{I}{U_{1_{t=n}}}\right) / (C'_1 - C_1),$$

where $K_{1_{t=0}}$ represents the electrical conductivity of the to-be-detected object, $\text{Area}_{t=0}$ represents the sectional area of the to-be-detected object when the impedance catheter is located at the bottom end of the to-be-detected object, $U_{1_{t=0}}$ represents the first voltage value when the impedance catheter is located at the bottom end of the to-be-detected object at a low frequency, and $U'_{1_{t=0}}$ represents the first voltage value when the impedance catheter is located at the bottom end of the to-be-detected object at a high frequency.

It should be noted that during the obtaining of the sectional area of each location of the to-be-detected object, noise processing may further be performed on transmission data, and the transmission data is the voltage value, current value, and the like that are directly obtained by the impedance catheter. A noise processing process is for example: using a high impedance signal source, and using an operational amplifier that has low temperature drift with a low noise voltage and a low noise current and has a wide band and high impedance as a pre-amplifier. Similarly, during an alternating constant current source conversion, a device having a similar function may be selected. Further, since detection is for weak signals whose signal-to-noise ratio is relatively low, in addition to that an analog circuit is elaborately deployed to extract a signal, denoising may further be performed on the signals by using an FFT algorithm, to resolve the problem of low signal-to-noise ratio. Therefore, not only hardware circuit costs are reduced, but also real-time stability of a detection system is ensured.

Further, the processing module 300 is further configured to: obtain at least one of the diameter stenosis, a plaque parameter, and a fractional flow reserve FFR of each location of the to-be-detected object by parsing the obtained sectional area. Further, a model of the to-be-detected object may further be drawn by obtaining the sectional area and the plaque parameter of each location of the to-be-detected object.

In an implementation of the present invention, the data processing module 300 is configured to: obtain the diameter stenosis of each location of the to-be-detected object according to the obtained cross-sectional area of each location of the to-be-detected object; and obtain the sectional diameter of each location of the to-be-detected object according to the cross-sectional area of each location of the to-be-detected object, so that the stenosis rate of each location of the to-be-detected object.

The sectional diameter of each location of the to-be-detected object is $$D_{t=n} = 2\sqrt{\frac{\text{Area}_{t=n} \times 4}{\pi}}.$$

Further, the diameter stenosis=(the sectional diameter of a normal location at an entrance of the to-be-detected object−the sectional diameter of a current location of the to-be-detected object)/the sectional diameter of the normal location at the entrance of the to-be-detected object*100%.

It may be understood that the diameter stenosis of the current location of the blood vessel determined in this implementation is obtained when the impedance catheter is located at the bottom end of the blood vessel. Therefore, when the to-be-detected object is a blood vessel, the impedance catheter inserts as much as possible to a location where the blood vessel is in a normal state, and no details are described herein.

In an implementation of the present invention, the data processing module 300 is configured to obtain a plaque parameter of each location of the to-be-detected object according to the obtained cross-sectional area of each location of the to-be-detected object, and the voltage values obtained when the impedance catheter is located at each location of the to-be-detected object, where the plaque parameter is $$K_{t=n \cdot \Delta t} = \frac{I}{U_{12_{t=n}}} - \text{Area}_{t=n \cdot \Delta t} \cdot C_2.$$

It may be learned of according to the foregoing formula that a smaller value of the parameter K indicates higher content of fat in the wall of the blood vessel.

Certainly, in other implementations of the present invention, the cross-sectional area of each location of the blood vessel may further be obtained by means of imageology, for example, any imageological method such as CT, MM, and radiography, and no details are described herein.

In an implementation of the present invention, the data processing module 300 is configured to obtain a fractional flow reserve FFR of each location of the to-be-detected object according to the obtained cross-sectional area of each location of the to-be-detected object.

It may be understood that the cross-sectional area of each location of the to-be-detected object may also be obtained by means of imageology, for example, any imageological method such as CT, MRI, and radiography, and no details are described herein.

In this implementation, the data processing module 300 is specifically configured to classify the to-be-detected object into two regions according to the obtained cross-sectional area of each location of the to-be-detected object, where the two regions are respectively a normal region and a stenosis region.

In an implementation of the present invention, the data processing module 300 classifies corresponding locations of the to-be-detected object whose values of area stenosis are less than 50% into the normal region, and defines other locations as the stenosis region. Certainly, in other implementations of the present invention, a demarcation point or demarcation manner for the normal region and the stenosis region may be demarcated as required, and no details are described herein.

The area stenosis=(the sectional area of a normal location at an entrance of the to-be-detected object−a current sectional area)/the sectional area of the normal location at the entrance of the to-be-detected object*100%.

Further, to simplify a calculation process, the data processing module 300 considers two or more stenosis regions as the same stenosis region. In this implementation, a region classification threshold is set, and the region classification threshold is a length value. Whether a distance value between two neighboring stenosis regions is less than the region classification threshold is determined. If so, the neighboring two stenosis regions are considered as the same stenosis region.

The data processing module 300 is further configured to calculate a pressure gradient for each of the normal region and the stenosis region; and calculate integrals of the pressure gradient $\Delta P_{normal}$ for the normal region by using the Poiseuille formula.

That the data processing module 300 calculates a pressure gradient $\Delta P_{stenosis}$ for the stenosis region includes: performing virtual correction on a bending part of the to-be-detected object; and decomposing the to-be-detected object into a two-dimensional axial symmetric model according to the cross-sectional area of each location, to generate a structured grid. In this way, three-dimensional calculation of the stenosis region is converted to two-dimensional calculation of the stenosis region, so that a calculation speed is improved by thousands of times.

With reference to FIG. 3, in a specific example of the present invention, the data processing module 300 virtually straightens the to-be-detected object along an axial direction thereof, radially dissects the straightened to-be-detected object to obtain a symmetric surface P, and decomposes the symmetric surface P into two parts along its symmetric axis; and generates a two-dimensional symmetric model according to the sectional area of each location of the to-be-detected object, then generates a structured grid, and further, calculates a pressure gradient of the structured grid generated at either side of the symmetric axis.

In a specific example of the present invention, a contrast agent is injected for one time, and the data collection module 200 precisely measures a reference speed of a blood flow in the blood vessel by using the impedance catheter. The reference speed is a normal flowing speed of the blood flow and is represented by $V_b$. A causative drug is injected for one time, and the data collection module 200 precisely measures the blood flow speed by using the impedance catheter when the blood vessel is in a maximal congestion phase, and the blood flow speed in the maximal congestion phase is represented by $V_c$.

Certainly, the reference speed $V_b$ and the blood flow speed $V_c$ when the blood vessel is in the maximal congestion phase may also be obtained by using the radiography technology, and no details are described herein.

The data processing module 300 solves the momentum equation by using the finite difference method according to the momentum equation in the theory of fluid mechanics, and obtains the pressure gradient $\Delta P_{stenosis}$ of each location in the stenosis region; and solves the equation of continuity and the momentum equation by using the finite difference method according to the equation of continuity and the momentum equation in the theory of fluid mechanics, and obtains the pressure gradient $\Delta P_{stenosis}$ of each location in the stenosis region.

In this implementation, according to the law of conservation of mass and the law of conservation of momentum, in the two-dimensional axial symmetric blood vessel, the pressure gradient is calculated by using the standard finite difference method, to solve the following equation:

$$\frac{1}{r}\frac{\partial}{\partial r}(ru_r) + \frac{\partial u_z}{\partial z} = 0,$$

$$\rho\left(\frac{\partial u_r}{\partial t} + u_r\frac{\partial u_r}{\partial r} + u_z\frac{\partial u_r}{\partial z}\right) = -\frac{\partial p}{\partial r} + \mu\left[\frac{1}{r}\frac{\partial}{\partial r}\left(r\frac{\partial u_r}{\partial r}\right) + \frac{\partial^2 u_r}{\partial z^2} - \frac{u_r}{r^2}\right],$$

$$\rho\left(\frac{\partial u_z}{\partial t} + u_r\frac{\partial u_z}{\partial r} + u_z\frac{\partial u_z}{\partial z}\right) = -\frac{\partial p}{\partial z} + \mu\left[\frac{1}{r}\frac{\partial}{\partial r}\left(r\frac{\partial u_z}{\partial r}\right) + \frac{\partial^2 u_z}{\partial z^2}\right].$$

where ρ represents the density of blood, u_z, and u_r respectively represent flowing speeds in the z direction and in the r direction, μ represents the kinetic viscosity of the blood, and p represents the intensity of pressure of the blood.

Further, the data processing module 300 may correct the foregoing process based on an angle impact parameter prestored in a backend database. In this way, the pressure gradient $\Delta P_{stenosis}$ through the stenosis region may be precisely calculated.

Further, the data processing module 300 obtains the fractional flow reserve according to the obtained pressure gradient of the normal region and the stenosis region.

Upon introducing $\Delta P_{total} = \Sigma \Delta P_{normal} + \Sigma \Delta P_{stenosis}$, $$FFR = \frac{P_a - \Delta P_{total}}{P_a},$$

where FFR is the fractional flow reserve, $\Delta P_{total}$ is a sum of the pressure gradients of each location of the to-be-detected object, and $P_a$ is a constant. In this specific example, $P_a$ is the pressure of an aorta.

Further, the data processing module 300 may be configured to determine, according to a value of the FFR, whether a balloon dilation surgery needs to be carried out. For example, when FFR>0.75, the balloon dilation surgery does not need to be carried out; or when FFR≤0.75, the balloon dilation surgery needs to be carried out. Certainly, the value demarcation point is only exemplary and may be adjusted as required during actual application, and no details are described herein.

According to the coronary artery load detection system of the present invention, conventional three-dimensional calculation is converted into two-dimensional model calculation. Further, rapid calculation is performed on the value of the two-dimensional axial symmetric model to parse out the pressure gradient of the stenosis region, so as to obtain the fractional flow reserve FFR of each location in the blood vessel. Meanwhile, in a process of converting the three-dimensional calculation into the two-dimensional calculation, virtual correction is further performed on the bending part of the blood vessel, thereby greatly simplifying a calculation process and improving the calculation efficiency. It may be known through tests that a calculation time is <30 s, ensuring rapid diagnosis of the FFR in a process of radiography and interventional surgery.

It may be understood that in a specific application example of the present invention, whether a balloon dilation surgery needs to be carried out can be further determined based on the parameters such as the stenosis location, the plaque load, and the FFR that are obtained above, and the balloon dilation surgery is precisely carried out, thereby greatly reducing risks of the interventional surgery.

In an implementation of the present invention, the data processing module 300 is further configured to position the stenosis location of the blood vessel. The data processing module 300 draws a model of the to-be-detected object according to the obtained sectional area and the plaque parameter of each location of the to-be-detected object; and receives a positioning instruction, where the positioning instruction is to determine a positioning target for this time by using the model of the to-be-detected object.

The control module 100 drives the primary device for the second time to the bottom end of the to-be-detected object, and retraces the primary device for the second time at a constant retracement speed the same as that used in the previous time; and stops driving the primary device to move, when a parameter obtained by the primary device at the second time is the same as the positioning instruction.

In a specific application example of the present invention, if a current stopping location of the primary device is a stenosis location of the blood vessel, signals may be transmitted to a pressure pump (not shown). It should be noted that the pressure pump is also disposed in the impedance catheter, and the balloon dilation surgery is carried out by setting a pressure. In addition, a retracement action may further be performed on the impedance catheter once again to determine a dilation effect of a balloon on the blood vessel stenosis, and no details are described herein again.

In a specific example of the present invention, the sectional area and the plaque parameter of each location of the blood vessel are obtained according to the foregoing content to draw a model of the to-be-detected object, and the model is output to a display. A positioning target for this time is set, for example, a positioning instruction is input by using an external device such as a keyboard, or the positioning target for this time is positioned on the display by using an external device such as a mouse, to drive the impedance catheter for the second time to the bottom end of the to-be-detected object. The impedance catheter is retraced at a constant retracement speed the same as a speed used in the previous time, a measurement result of this time is output to the display according to the sectional area and the plaque parameter of each location of the blood vessel that are obtained by means of parsing. The measurement result of this time is compared with a measurement result of the previous time. If the impedance catheter reaches the location of the positioning target for this time, driving of the impedance catheter stops, and precise positioning is further performed.

Figure 4:
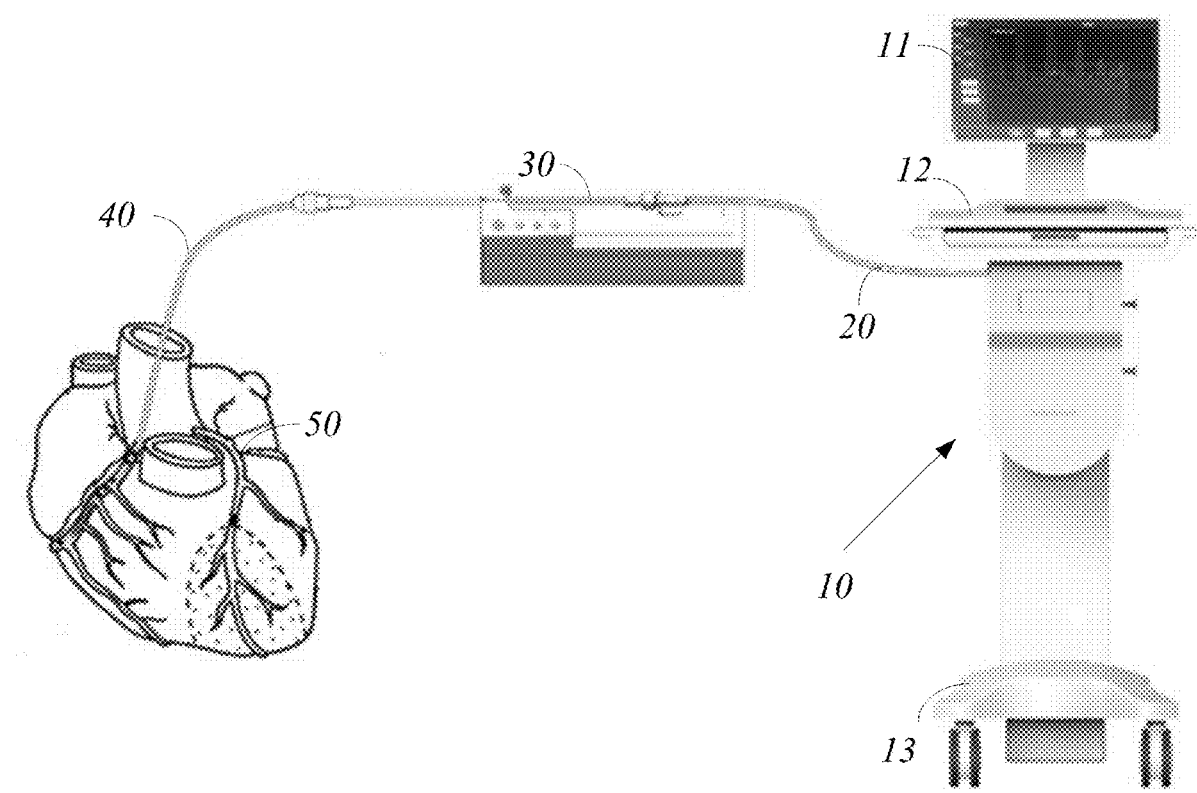
FIG. 4 is a schematic structural diagram of a coronary artery load detection system according to a specific example of the present invention.

With reference to FIG. 4, which is a schematic structural diagram of a coronary artery load detection system according to a specific implementation of the present invention, the system is configured to detect various parameters of a blood vessel 50 and includes a hardware part and a software part. The hardware part includes: a diagnosis instrument 10, and a connection line 20, a retracement motor 30, and an impedance catheter 40 that are sequentially connected to the diagnosis instrument 10. A display 11, an operation console 12, and a mobile support 13, and the like are disposed on the diagnosis instrument 10. The hardware part further includes: an analog front-end (not shown), an A/D convertor (not shown), an FPGA circuit (not shown), an ARM processor (not shown), and the like. The software part mainly includes: an upper computer program and a lower computer program. It can be understood that the functions of the control module 100, the data collection module 200, and the data processing module 300 can be integrated into the system, and no details are described herein.

In conclusion, according to the coronary artery load detection system and method of the present invention, a voltage value of each location of a to-be-detected object is obtained in a frequency conversion mode, so that the sectional area of each location of the to-be-detected object is obtained by means of parsing. Further, during parsing of the voltage value, an optimum voltage value of a known loop can be obtained by performing linear interpolation on a voltage value across two end of the loop, and an impact of a plaque existing in a blood vessel on the parsing result is eliminated. Still further, the sectional area of each location of the to-be-detected object is parsed, to obtain the diameter stenosis, a plaque parameter, and a fractional flow reserve FFR of each location of the to-be-detected object, and a model of the to-be-detected object can be drawn by obtaining the sectional area and the plaque parameter of each location of the to-be-detected object. During implementation of the system and the method, provided that an impedance catheter is retraced at a constant speed for only one time, the sectional area of each location in the blood vessel can be precisely learned of, and the diameter stenosis of each location is further obtained, thereby greatly simplifying an operation and processing process and reducing the detection costs.

For the ease of description, the foregoing apparatus is descried from the perspective of various modules separately according to functions thereof. Certainly, during implementation of this application, the functions of the various modules may be implemented in the same or multiple software and/or hardware.

It may be learned of from the description of the foregoing implementations that, a person skilled in the art may clearly understand that this application may be implemented by software in addition to a necessary general hardware platform. Based on such an understanding, the technical solutions of this application essentially or the part contributing to the prior art may be implemented in the form of a software product. The software product can be stored in a storage medium, such as a ROM/RAM, a magnetic disk, or an optical disc, and includes several instructions for instructing a computer device (which may be a personal computer, a server for pushing information, a network device, or the like) to perform the methods described in the implementations or some parts of the implementations of this application.

The apparatus implementations described above are merely exemplary. The modules described as separate components may be or may not be physically separate, and the components displayed as modules may be or may not be physical modules. That is, the modules may be located at one place or scattered on several network modules. Some or all of the modules may be selected according to actual requirements to achieve the objectives of the solutions of the implementations. A person of ordinary skill in the art can understand and implement the apparatus without creative efforts.

This application may be applicable to environments or configurations of multiple universal or dedicated computing systems. For example: a personal computer, a server computer for pushing information, a handheld device or a portable device, a flat panel device, a multi-processing module system, a microprocessing module-based system, a set-top box, a network PC, a microcomputer, a mainframe computer, and a distributed-computing environment including any one of the foregoing system or device.

This application can be described in the general context of computer-executable instructions executed by a computer, for example, a program module. Generally, the program unit includes a routine, program, object, component, data structure, and the like for executing a particular task or implementing a particular abstract data type. This application may also be practiced in distributed computing environments in which tasks are performed by remote processing devices that are connected by using a communications network. In a distributed computing environment, program modules may be located in both local and remote computer storage medium including storage device.

It should be understood that although this specification is described according to implementations, not each implementation merely includes an independent technical solution, and this specification is described in such a manner merely for the purpose of clarity. A person skilled in the art should take this specification as a whole, and the technical solutions in all the implementations can also be properly combined, to form other implementations that can be understand by a person skilled in the art.

A series of detailed description listed above is merely specific description of feasible implementations of the present invention, but is not intended to limit the protection scope of the present invention. Equivalent implementations or alternations made without departing from the spirit of the present invention shall fall within the protection scope of the present invention.

What is claimed is:

1. A coronary artery load detection method, characterized in that the method comprises:
   S1. obtaining a cross-sectional area of a reference cavity, and separately obtaining voltage values of a primary device at a location corresponding to the cross-sectional area of the reference cavity in a low frequency state and a high frequency state;
   S2. separately obtaining voltage values of the primary device at the location of a bottom end of a blood vessel in the low frequency state and the high frequency state under a same current;
   S3. driving the primary device to move at a constant speed, and obtaining voltage values of the primary device during the movement in the low frequency state under the same current;
   S4. obtaining a cross-sectional area of each location of the blood vessel according to a preset fixed current value, the cross-sectional area of the reference cavity, and the voltage values obtained by means of the steps S1, S2 and S3; and
   S5. obtaining a fractional flow reserve of each location of the blood vessel according to the obtained cross-sectional area of each location of the blood vessel;
   wherein step S5 comprises:
      classifying the blood vessel into two regions according to the obtained cross-sectional area of each location of the blood vessel, wherein the two regions are respectively: a no stenosis region and a stenosis region;
      calculating a pressure gradient for each of the no stenosis region and the stenosis region; and
      calculating integrals of a pressure gradient $\Delta P_{normal}$ for the no stenosis region by using the Poiseuille formula; and
   calculating a pressure gradient $\Delta P_{stenosis}$ for the stenosis region, wherein the step of calculating the pressure gradient $\Delta P_{stenosis}$ for the stenosis region comprises:
      performing converting a three-dimensional calculation of the stenosis region to a two-dimensional calculation on a bending part of the blood vessel;
      decomposing the blood vessel into a two-dimensional axial symmetric model according to the cross-sectional area of each location of the blood vessel, to generate a pressure graph;
      solving an equation of continuity and a momentum equation by using a finite difference method according to the equation of continuity and the momentum equation in a theory of fluid mechanics, and obtaining the pressure gradient $\Delta P_{stenosis}$ of each location in the stenosis region; and
      obtaining the fractional flow reserve according to the calculated pressure gradients of the no stenosis region and the stenosis region, the fractional flow reserve $$FFR = \frac{P_a - \Delta P_{total}}{P_a},$$

$\Delta P_{total} = \Sigma \Delta P_{normal} + \Sigma P_{stenosis}$,
wherein FFR is the fractional flow reserve, $\Delta P_{total}$ is a sum of the pressure gradients of each location of the blood vessel, and $P_a$ is a constant; and
wherein after the step S4, the method further comprises:
obtaining a plaque parameter of each location of the blood vessel according to the obtained cross-sectional area of each location of the blood vessel, and the voltage values obtained when the primary device is located at each location of the blood vessel,
wherein the plaque parameter is $$K_{t=n \cdot \Delta t} = \frac{I}{U_{12_{t=n}}} - \text{Area}_{t=n \cdot \Delta t} \cdot C_2,$$

in the plaque parameter, $K_{t=n \cdot \Delta t}$ represents an electrical conductivity of the blood vessel at a time point t, I represents a preset fixed current value, $U_{12_{t=n}}$ represents a third voltage value of the blood vessel at the time point t, $\text{Area}_{t=n \cdot \Delta t}$ represents the cross-sectional area of each location of the blood vessel at the time point t, and $C_2$ is a constant;
wherein the method further comprises drawing a model of the blood vessel according to the obtained cross-sectional area of each location of the blood vessel and the plaque parameter of each location of the blood vessel; and
wherein the method further comprises:
receiving a positioning instruction, wherein the positioning instruction is to determine a positioning target for a period of time by using the model of the blood vessel;
driving the primary device to move for a second time to the bottom end of the blood vessel, and retracing the primary device for a first time at a constant retracement speed the same as that used in the period of time; and
stopping the step of driving the primary device to move after the second time, when a parameter obtained by the primary device at the second time is the same as the positioning instruction.

2. The coronary artery load detection method according to claim 1, characterized in that:
the primary device is an impedance catheter, and the impedance catheter comprises: a balloon catheter, a first signal emission terminal disposed at a far end of the balloon catheter, a second signal emission terminal disposed at an end of the balloon catheter, and three measurement terminals that are equally spaced and that are disposed between the first signal emission terminal and the second signal emission terminal on the balloon catheter, two of the three measurement terminals forming a loop with the first signal emission terminal and the second signal emission terminal;
the three measurement terminals comprise: a first measurement terminal D, a second measurement terminal E and a third measurement terminal F that are sequentially disposed at a location between the first signal emission terminal to the second signal emission terminal, wherein the distance between the first measurement terminal D and the second measurement terminal E is equal to the distance between the second measurement terminal E and the third measurement terminal F;
a D-E loop is formed between the first measurement terminal D and the second measurement terminal E, an E-F loop is formed between the second measurement terminal E and the third measurement terminal F, and a D-F loop is formed between the first measurement terminal D and the third measurement terminal F; and
the voltage values comprise: a first voltage value corresponding to the D-E loop, a second voltage value corresponding to the D-F loop, and a third voltage value corresponding to the E-F loop.

3. The coronary artery load detection method according to claim 2, characterized in that:
the step S4 specifically comprises: processing the voltage values obtained by means of the step S1 and the cross-sectional area of the reference cavity, to obtain a constant C by dividing an electrical conductivity of a liquid flowing in the blood vessel by an effective length between two corresponding measurement terminals; and
the following are obtained when the primary device is in the low frequency state:

$$C_1 = \frac{1}{U_1 \cdot \text{Area}_{IC}}, C_2 = \frac{1}{U_{12} \cdot \text{Area}_{IC}}, C_3 = \frac{1}{U_2 \cdot \text{Area}_{IC}},$$

$$C_1 = C_2 = 2C_3,$$

wherein I represents the preset fixed current value; a constant $C_1$, a constant $C_2$, and a constant $C_3$ are respectively obtained by dividing the electrical conductivity of the liquid flowing in the blood vessel by the effective length between the two corresponding measurement terminals when the impedance catheter is in the blood vessel in the low frequency state, $\text{Area}_{IC}$ represents the cross-sectional area of the reference cavity, $U_1$ represents the first voltage value, $U_2$ represents the second voltage value, $U_{12}$ represents the third voltage value, both $U_1$ and $U_2$ are directly obtained by using the impedance catheter, and $U_{12}$ is calculated by using $U_1$ and $U_2$, wherein $U_{12} = U_2 - U_1$; or
the following are obtained when the primary device is in the high frequency state:

$$C'_1 = \frac{I}{U'_1 \cdot \text{Area}_{IC}}, C'_2 = \frac{I}{U'_{12} \cdot \text{Area}_{IC}}, C'_3 = \frac{I}{U'_2 \cdot \text{Area}_{IC}},$$

$$C'_1 = C'_2 = 2C'_3,$$

wherein a constant $C'_1$, a constant $C'_2$, and a constant $C'_3$ are respectively obtained by dividing the electrical conductivity of the liquid flowing in the blood vessel by the effective length between the two corresponding measurement terminals when the impedance catheter is in the blood vessel in the high frequency state, $\text{Area}_{IC}$ represents the cross-sectional area of the reference cavity, $U'_1$ represents the first voltage value, $U'_2$ represents the second voltage value, $U'_{12}$ represents the third voltage value, both $U'_1$ and $U'_2$ are directly obtained by using the impedance catheter, and $U'_{12}$ is calculated by using $U'_1$ and $U'_2$, wherein $U'_{12} = U'_2 - U'_1$.

4. The coronary artery load detection method according to claim 3, characterized in that:

the step S4 specifically comprises: obtaining, according to the constant C obtained after the processing and the voltage values obtained by means of the step S2, the cross-sectional area of the blood vessel when the impedance catheter is located at the bottom end of the blood vessel; and the following is obtained when the primary device is in the low frequency state:

$$\frac{I}{U_{1_{t=0}}} - \text{Area}_{t=0} \cdot C_1 = K_{1_{t=0}};$$

or the following is obtained when the primary device is in the high frequency state:

$$\frac{I}{U'_{1_{t=0}}} - \text{Area}_{t=0} \cdot C'_1 = K_{1_{t=0}};$$

so that when the impedance catheter is located at the bottom end of the blood vessel, the sectional area of the blood vessel is:

$$\text{Area}_{t=0} = \left(\frac{I}{U'_{1_{t=0}}} - \frac{I}{U_{1_{t=0}}}\right) \bigg/ (C'_1 - C_1),$$

wherein $K_{1_{t=0}}$ represents the electrical conductivity of the blood vessel, $\text{Area}_{t=0}$ represents the cross-sectional area of the blood vessel when the impedance catheter is located at the bottom end of the blood vessel, $U_{1_{t=0}}$ represents the first voltage value when the impedance catheter is located at the bottom end of the blood vessel at the low frequency, and $U'_{1_{t=0}}$ represents the first voltage value when the impedance catheter is located at the bottom end of the blood vessel at the high frequency.

5. The coronary artery load detection method according to claim 4, characterized in that:

at a time point $t = n \cdot \Delta t$, a distance difference between a current location of the impedance catheter and the location of the bottom end of the blood vessel at which the impedance catheter is located is: $L = V \cdot n \cdot \Delta t$, wherein L represents a distance difference, V represents a retracement speed of the impedance catheter, n represents a positive integer, and $\Delta t$ represents a time difference;

the step S4 further comprises: performing linear interpolation on the cross-sectional area of each location of the blood vessel $\text{Area}_{t=(n-1) \cdot \Delta t}$ corresponding to the D-E loop and the cross-sectional area $\text{Area}_{t=n \cdot \Delta t}$ of the blood vessel corresponding to the E-F loop, to obtain the cross-sectional area of each location of the blood vessel corresponding to the D-F loop:

$$\frac{\text{Area}_{t=(n-1) \cdot \Delta t} \cdot C_1 + \text{Area}_{t=n \cdot \Delta t} \cdot C_2}{C_1 + C_2}$$

and the following are obtained when the primary device is in the low frequency state:

$$\frac{I}{U_{1_{t=n}}} - \text{Area}_{t=(n-1) \cdot \Delta t} \cdot C_1 = K_{1_{t=n \cdot \Delta t}},$$

$$\frac{I}{U_{12_{t=n}}} - \text{Area}_{t=(n-1) \cdot \Delta t} \cdot C_2 = K_{2_{t=n \cdot \Delta t}},$$

$$\frac{I}{U_{2_{t=n}}} - \frac{\text{Area}_{t=(n-1) \cdot \Delta t} \cdot C_1 + \text{Area}_{t=n \cdot \Delta t} \cdot C_2}{C_1 + C_2} \cdot C_3 = \frac{1}{\frac{1}{K_{1_{t=n \cdot \Delta t}}} + \frac{1}{K_{2_{t=n \cdot \Delta t}}}},$$

the following can be obtained upon introducing $C_1 = C_2 = 2C_3$:

$$\frac{I}{U_{1_{t=n}}} - \text{Area}_{t=(n-1) \cdot \Delta t} \cdot 2C_3 = K_{1_{t=n \cdot \Delta t}},$$

$$\frac{I}{U_{12_{t=n}}} - \text{Area}_{t=(n-1) \cdot \Delta t} \cdot 2C_3 = K_{2_{t=n \cdot \Delta t}},$$

$$\frac{I}{U_{2_{t=n}}} - \frac{\text{Area}_{t=(n-1) \cdot \Delta t} + \text{Area}_{t=n \cdot \Delta t}}{2} \cdot C_3 = \frac{1}{\frac{1}{K_{1_{t=n \cdot \Delta t}}} + \frac{1}{K_{2_{t=n \cdot \Delta t}}}},$$

so that, $$C_3 \cdot (\text{Area}_{t=n \cdot \Delta t})^2 +$$
$$\left(\frac{3}{2} \cdot \frac{I}{U_{1_{t=n}}} - \frac{1}{2} \cdot \frac{I}{U_{12_{t=n}}} - 2 \cdot \frac{I}{U_{2_{t=n}}} - 2 \cdot C_3 \cdot \text{Area}_{t=(n-1) \cdot \Delta t}\right) \cdot \text{Area}_{t=n \cdot \Delta t} +$$
$$\left(\frac{3}{2} \cdot \frac{I}{U_{12_{t=n}}} - \frac{1}{2} \cdot \frac{1}{U_{1_{t=n}}} - 2 \cdot \frac{1}{U_{2_{t=n}}} + C_3 \cdot \text{Area}_{t=(n-1) \cdot \Delta t}\right) \cdot$$
$$\text{Area}_{t=(n-1) \cdot \Delta t} = 0$$

defining:

$$B_3 = \left(\frac{3}{2} \cdot \frac{1}{U_{1_{t=n}}} - \frac{1}{2} \cdot \frac{I}{U_{12_{t=n}}} - 2 \cdot \frac{I}{U_{2_{t=n}}} - 2 \cdot C_3 \cdot \text{Area}_{t=(n-1) \cdot \Delta t}\right),$$

$$A_3 = \left(\frac{3}{2} \cdot \frac{I}{U_{12_{t=n}}} - \frac{1}{2} \cdot \frac{I}{U_{1_{t=n}}} - 2 \cdot \frac{I}{U_{2_{t=n}}} + C_3 \cdot \text{Area}_{t=(n-1) \cdot \Delta t}\right) \cdot \text{Area}_{t=(n-1) \cdot \Delta t}$$

when the value of $$\frac{I}{U_{12_{t=n}}}$$

gradually increases, the cross-sectional area of each location of the blood vessel is:

$$\text{Area}_{t=n \cdot \Delta t} = \frac{-B_3 + \sqrt{B_3^2 - 4 \cdot C_3 \cdot A_3}}{2 \cdot C_3},$$

or when the value of $$\frac{I}{U_{12_{t=n}}}$$

gradually decreases, the cross-sectional area of each location of the blood vessel is:

$$Area_{t=n\cdot\Delta t} = \frac{-B_3 - \sqrt{B_3^2 - 4\cdot C_3 \cdot A_3}}{2\cdot C_3},$$

wherein $Area_{t=n\cdot\Delta t}$ represents the cross-sectional area of each location of the blood vessel at the time point t, $K_{1_{t=n\cdot\Delta t}}$ represents the electrical conductivity of the blood vessel corresponding to the D-E loop at the time point t, $K_{2_{t=n\cdot\Delta t}}$ represents the electrical conductivity of the blood vessel corresponding to the E-F loop at the time point t, $U_{1_{t=n}}$ represents the first voltage value of the blood vessel corresponding to the D-E loop at the time point t, $U_{2_{t=n}}$ represents the second voltage value of the blood vessel corresponding to the E-F loop at the time point t, and $U_{12_{t=n}}$ represents the third voltage value of the blood vessel corresponding to the E-F loop at the time point t.

6. The coronary artery load detection method according to claim 1, characterized in that: after the step S4, the method further comprises:
obtaining a diameter stenosis of each location of the blood vessel according to the obtained cross-sectional area of each location of the blood vessel, and the diameter stenosis=(a sectional diameter of an initial location at an entrance of the blood vessel−a sectional diameter of a current location of the blood vessel)/the sectional diameter of the initial location at the entrance of the blood vessel*100%.

7. A coronary artery load detection system, characterized in that: the system comprises a control module, a data collection module, and a data processing module;
the data collection module is configured to: obtain a cross-sectional area of a reference cavity, and separately obtain voltage values of a primary device at a location corresponding to the cross-sectional area of the reference cavity in a low frequency state and a high frequency state; and
separately obtain voltage values of the primary device at the location of a bottom end of a blood vessel in the low frequency state and the high frequency state under a same current;
the control module is configured to drive the primary device to move at a constant speed, and the data collection module is further configured to: obtain voltage values of the primary device during the movement in the low frequency state under the same current;
the data processing module is configured to obtain a cross-sectional area of each location of the blood vessel according to a preset fixed current value, the cross-sectional area of the cavity, and the obtained voltage values;
the data processing module is further configured to:
obtain a fractional flow reserve of each location of the blood vessel according to the obtained cross-sectional area of each location of the blood vessel;
the data processing module is further configured to: classify the blood vessel into two regions according to the obtained cross-sectional area of each location of the blood vessel, wherein the two regions are respectively: a no stenosis region and a stenosis region;
calculate a pressure gradient for each of the no stenosis region and the stenosis region; and calculate integrals of a pressure gradient $\Delta P_{normal}$ for the no stenosis region by using the Poiseuille formula; and
calculate a pressure gradient $\Delta P_{stenosis}$ for the stenosis region, the step of calculate the pressure gradient $\Delta P_{stenosis}$ for the stenosis region comprises:
performing converting a three-dimensional calculation of the stenosis region to a two-dimensional calculation on a bending part of the blood vessel;
decomposing the blood vessel into a two-dimensional axial symmetric model according to the cross-sectional area of each location of the blood vessel, to generate a structured grid;
solving an equation of continuity and a momentum equation by using a finite difference method according to the equation of continuity and the momentum equation in a theory of fluid mechanics, and obtaining the pressure gradient $\Delta P_{stenosis}$ of each location in the stenosis region; and
obtaining the fractional flow reserve according to the calculated pressure gradients of the no stenosis region and the stenosis region,
the fractional flow reserve $$FFR = \frac{P_a - \Delta P_{total}}{P_a}, \Delta P_{total} = \sum \Delta P_{normal} + \sum \Delta P_{stenosis},$$

wherein FFR is the fractional flow reserve, $\Delta P_{total}$ is a sum of the pressure gradient of each location of the blood vessel, and $P_a$ is a constant; and
the data processing module is further configured to:
obtain a plaque parameter of each location of the blood vessel according to the obtained cross-sectional area of each location of the blood vessel, and the voltage values obtained when the primary device is located at each location of the blood vessel,
wherein the plaque parameter is $$K_{t=n\cdot\Delta t} = \frac{1}{U_{12_{t=n}}} - Area_{t=n\cdot\Delta t} \cdot C_2,$$

in the plaque parameter, $K_{t=n\cdot\Delta t}$ represents an electrical conductivity of the blood vessel at a time point t, I represents a preset fixed current value, $U_{12_{t=n}}$ represents a third voltage value of the blood vessel at the time point t, $Area_{t=n\cdot\Delta t}$ represents the cross-sectional area of each location of the blood vessel at the time point t, and $C_2$ is a constant;
wherein the data processing module is further configured to: draw a model of the blood vessel according to the obtained cross-sectional area of each location of the blood vessel and the plaque parameter of each location of the blood vessel; and receive a positioning instruction, wherein the positioning instruction is to determine a positioning target for a period of time by using the model of the blood vessel; and
wherein the control module is further configured to: drive the primary device to move for a second time to the bottom end of the blood vessel, and retrace the primary device for a first time at a constant retracement speed the same as that used in the period of time; and stop the driving of the primary device to move after the second time, when a parameter obtained by the primary device at the second time is the same as the positioning instruction.

8. The coronary artery load detection system according to claim 7, characterized in that:

the primary device is an impedance catheter, and the impedance catheter comprises: a balloon catheter, a first signal emission terminal disposed at a far end of the balloon catheter, a second signal emission terminal disposed at an end of the balloon catheter, and three measurement terminals that are equally spaced and that are disposed between the first signal emission terminal and the second signal emission terminal on the balloon catheter, two of the three measurement terminals forming a loop with the first signal emission terminal and the second signal emission terminal;

the three measurement terminals comprise: a first measurement terminal D, a second measurement terminal E and a third measurement terminal F that are sequentially disposed at a location between the first signal emission terminal to the second signal emission terminal, wherein the distance between the first measurement terminal D and the second measurement terminal E is equal to the distance between the second measurement terminal E and the third measurement terminal F;

a D-E loop is formed between the first measurement terminal D and the second measurement terminal E, an E-F loop is formed between the second measurement terminal E and the third measurement terminal F, and a D-F loop is formed between the first measurement terminal D and the third measurement terminal F; and the voltage values comprise: a first voltage value corresponding to the D-E loop, a second voltage value corresponding to the D-F loop, and a third voltage value corresponding to the E-F loop.

9. The coronary artery load detection system according to claim 8, characterized in that:

the data processing module is specifically configured to: process the voltage values and the cross-sectional area of the reference cavity, to obtain a constant C by dividing an electrical conductivity of a liquid flowing in the blood vessel by an effective length between two corresponding measurement terminals; and the following are obtained when the primary device is in the low frequency state:

$$C_1 = \frac{1}{U_1 \cdot \text{Area}_{IC}}, C_2 = \frac{1}{U_{12} \cdot \text{Area}_{IC}}, C_3 = \frac{1}{U_2 \cdot \text{Area}_{IC}},$$

$$C_1 = C_2 = 2C_3,$$

wherein I represents the preset fixed current value; a constant $C_1$, a constant $C_2$, and a constant $C_3$ are respectively obtained by dividing the electrical conductivity of the liquid flowing in the blood vessel by the effective length between the two corresponding measurement terminals when the impedance catheter is in the blood vessel in the low frequency state, $\text{Area}_{IC}$ represents the cross-sectional area of the reference cavity, $U_1$ represents the first voltage value, $U_2$ represents the second voltage value, $U_{12}$ represents the third voltage value, both $U_1$ and $U_2$ are directly obtained by using the impedance catheter, and $U_{12}$ is calculated by using $U_1$ and $U_2$, wherein $U_{12}=U_2-U_1$; or the following are obtained when the primary device is in the high frequency state:

$$C'_1 = \frac{1}{U'_1 \cdot \text{Area}_{IC}}, C'_2 = \frac{1}{U'_{12} \cdot \text{Area}_{IC}}, C'_3 = \frac{1}{U'_2 \cdot \text{Area}_{IC}},$$

$$C'_1 = C'_2 = 2C'_3,$$

wherein a constant $C'_1$, a constant $C'_2$, and a constant $C'_3$ are respectively obtained by dividing the electrical conductivity of the liquid flowing in the blood vessel by the effective length between two corresponding measurement terminals when the impedance catheter is in the blood vessel in the high frequency state, $\text{Area}_{IC}$ represents the cross-sectional area of the reference cavity, $U'_1$ represents the first voltage value, $U'_2$ represents the second voltage value, $U'_{12}$ represents the third voltage value, both $U'_1$ and $U'_2$ are directly obtained by using the impedance catheter, and $U'_{12}$ is calculated by using $U'_1$ and $U'_2$, wherein $U'_{12}=U'_2-U'_1$.

10. The coronary artery load detection system according to claim 9, characterized in that:

the data processing module is specifically configured to: obtain, according to the constant C obtained after the processing and the obtained voltage values, the cross-sectional area of the blood vessel when the impedance catheter is located at the bottom end of the blood vessel; and the following is obtained when the primary device is in the low frequency state:

$$\frac{I}{U_{1_{t=0}}} - \text{Area}_{t=0} \cdot C_1 = K_{1_{t=0}};$$

or the following is obtained when the primary device is in the high frequency state:

$$\frac{I}{U'_{1_{t=0}}} - \text{Area}_{t=0} \cdot C'_1 = K_{1_{t=0}};$$

so that when the impedance catheter is located at the bottom end of the blood vessel, the sectional area of the blood vessel is:

$$\text{Area}_{t=0} = \left(\frac{I}{U'_{1_{t=0}}} - \frac{I}{U_{1_{t=0}}}\right) / (C'_1 - C_1),$$

wherein $K_{1_{t=0}}$ represents the electrical conductivity of the blood vessel, $\text{Area}_{t=0}$ represents the cross-sectional area of the blood vessel when the impedance catheter is located at the bottom end of the blood vessel, $U_{1_{t=0}}$ represents the first voltage value when the impedance catheter is located at the bottom end of the blood vessel at the low frequency, and $U'_{1_{t=0}}$ represents the first voltage value when the impedance catheter is located at the bottom end of the blood vessel at the high frequency.

11. The coronary artery load detection system according to claim 10, characterized in that:

at a time point $t=n\cdot\Delta t$, a distance difference between a current location of the impedance catheter and the location of the bottom end of the blood vessel at which the impedance catheter is located is: $L=V\cdot n\cdot\Delta t$, wherein L represents a distance difference, V represents a retracement speed of the impedance catheter, n represents a positive integer, and $\Delta t$ represents a time difference;

the data processing module is further configured to perform linear interpolation on the cross-sectional area of each location of the blood vessel $\text{Area}_{t=(n-1)\cdot\Delta t}$ corresponding to the D-E loop and the cross-sectional area $\text{Area}_{t=n\cdot\Delta t}$ of the blood vessel corresponding to the E-F loop, to obtain the cross-sectional area of the blood vessel corresponding to the D-F loop:

$$\frac{\text{Area}_{t=(n-1)\cdot\Delta t}\cdot C_1 + \text{Area}_{t=n\cdot\Delta t}\cdot C_2}{C_1 + C_2};$$

and the following are obtained when the primary device is in the low frequency state:

$$\frac{I}{U_{1_{t=n}}} - \text{Area}_{t=(n-1)\cdot\Delta t}\cdot C_1 = K_{1_{t=n\cdot\Delta t}},$$

$$\frac{I}{U_{12_{t=n}}} - \text{Area}_{t=n\cdot\Delta t}\cdot C_2 = K_{2_{t=n\cdot\Delta t}},$$

$$\frac{I}{U_{2_{t=n}}} - \frac{\text{Area}_{t=(n-1)\cdot\Delta t}\cdot C_1 + \text{Area}_{t=n\cdot\Delta t}\cdot C_2}{C_1 + C_2}\cdot C_3 = \frac{1}{\frac{1}{K_{1_{t=n\cdot\Delta t}}} + \frac{1}{K_{2_{t=n\cdot\Delta t}}}},$$

the following can be obtained upon introducing $C_1 = C_2 = 2C_3$:

$$\frac{I}{U_{1_{t=n}}} - \text{Area}_{t=(n-1)\cdot\Delta t}\cdot 2C_3 = K_{1_{t=n\cdot\Delta t}},$$

$$\frac{I}{U_{12_{t=n}}} - \text{Area}_{t=n\cdot\Delta t}\cdot 2C_3 = K_{2_{t=n\cdot\Delta t}},$$

$$\frac{I}{U_{2_{t=n}}} - \frac{\text{Area}_{t=(n-1)\cdot\Delta t} + \text{Area}_{t=n\cdot\Delta t}}{2}\cdot C_3 = \frac{1}{\frac{1}{K_{1_{t=n\cdot\Delta t}}} + \frac{1}{K_{2_{t=n\cdot\Delta t}}}},$$

so that $$C_3\cdot(\text{Area}_{t=n\cdot\Delta t})^2 +$$

$$\left(\frac{3}{2}\cdot\frac{I}{U_{1_{t=n}}} - \frac{1}{2}\cdot\frac{I}{U_{12_{t=n}}} - 2\cdot\frac{I}{U_{2_{t=n}}} - 2\cdot C_3\cdot\text{Area}_{t=(n-1)\cdot\Delta t}\right)\cdot\text{Area}_{t=n\cdot\Delta t} +$$

$$\left(\frac{3}{2}\cdot\frac{I}{U_{12_{t=n}}} - \frac{1}{2}\cdot\frac{I}{U_{1_{t=n}}} - 2\cdot\frac{I}{U_{2_{t=n}}} + C_3\cdot\text{Area}_{t=(n-1)\cdot\Delta t}\right)\cdot$$

$$\text{Area}_{t=(n-1)\cdot\Delta t} = 0,$$

defining:

$$B_3 = \left(\frac{3}{2}\cdot\frac{I}{U_{1_{t=n}}} - \frac{1}{2}\cdot\frac{I}{U_{12_{t=n}}} - 2\cdot\frac{I}{U_{2_{t=n}}} - 2\cdot C_3\cdot\text{Area}_{t=(n-1)\cdot\Delta t}\right),$$

$$A_3 = \left(\frac{3}{2}\cdot\frac{I}{U_{12_{t=n}}} - \frac{1}{2}\cdot\frac{I}{U_{1_{t=n}}} - 2\cdot\frac{I}{U_{2_{t=n}}} + C_3\cdot\text{Area}_{t=(n-1)\cdot\Delta t}\right)\cdot\text{Area}_{t=(n-1)\cdot\Delta t};$$

when the value of $$\frac{I}{U_{12_{t=n}}}$$

gradually increases, the cross-sectional area of each location of the blood vessel is:

$$\text{Area}_{t=n\cdot\Delta t} = \frac{-B_3 + \sqrt{B_3^2 - 4\cdot C_3\cdot A_3}}{2\cdot C_3},$$

or when the value of $$\frac{I}{U_{12_{t=n}}}$$

gradually decreases, the cross-sectional area of each location of the blood vessel is:

$$\text{Area}_{t=n\cdot\Delta t} = \frac{-B_3 - \sqrt{B_3^2 - 4\cdot C_3\cdot A_3}}{2\cdot C_3}$$

wherein $\text{Area}_{t=n\cdot\Delta t}$ represents the cross-sectional area of each location of the blood vessel at the time point t, $K_{1_{t=n\cdot\Delta t}}$ represents the electrical conductivity of the blood vessel corresponding to the D-E loop at the time point t, $K_{2_{t=n\cdot\Delta t}}$ represents the electrical conductivity of the blood vessel corresponding to the E-F loop at the time point t, $U_{1_{t=n}}$ represents the first voltage value of the blood vessel corresponding to the D-E loop at the time point t, $U_{2_{t=n}}$ represents the second voltage value of the blood vessel corresponding to the E-F loop at the time point t, and $U_{12_{t=n}}$ represents the third voltage value of the blood vessel corresponding to the E-F loop at the time point t.

12. The coronary artery load detection system according to claim 7, characterized in that: the data processing module is further configured to:

obtain a diameter stenosis of each location of the blood vessel according to the obtained cross-sectional area of each location of the blood vessel, and the diameter stenosis=(a sectional diameter of an initial location at an entrance of the blood vessel−a sectional diameter of a current location of the blood vessel)/the sectional diameter of the initial location at the entrance of the blood vessel*100%.

\* \* \* \* \*